(12) United States Patent
Krenzel

(10) Patent No.: US 9,668,902 B1
(45) Date of Patent: Jun. 6, 2017

(54) SELECTIVELY ADJUSTABLE ARM AND SHOULDER SUPPORT

(71) Applicant: Ronald Louis Krenzel, Longmont, CO (US)

(72) Inventor: Ronald Louis Krenzel, Longmont, CO (US)

(*) Notice: Subject to any disclaimer, the term of this patent is extended or adjusted under 35 U.S.C. 154(b) by 0 days.

(21) Appl. No.: 14/849,441

(22) Filed: Sep. 9, 2015

Related U.S. Application Data

(63) Continuation-in-part of application No. 14/253,343, filed on Apr. 15, 2014.

(51) Int. Cl.
*A61F 5/01* (2006.01)

(52) U.S. Cl.
CPC ............ *A61F 5/0118* (2013.01); *A61F 5/013* (2013.01); *A61F 2005/0172* (2013.01)

(58) Field of Classification Search
CPC ...................................................... A61F 5/0118
See application file for complete search history.

(56) References Cited

U.S. PATENT DOCUMENTS

| | | |
|---|---|---|
| 890,842 A | 6/1908 | Cheatham |
| 1,267,142 A | 5/1918 | Stowers et al. |
| 1,304,153 A | 5/1919 | Bugge |
| 2,187,323 A | 1/1940 | Kelton et al. |
| 2,358,551 A | 9/1944 | Beaton |
| 2,811,349 A | 10/1957 | Bondurant et al. |
| 3,000,378 A | 9/1961 | Zieman |
| 3,338,236 A | 8/1967 | McLeod, Jr. |
| 3,404,680 A | 10/1968 | Guttman et al. |
| 3,815,588 A | 6/1974 | Klausner |
| 4,188,944 A | 2/1980 | Augustyniak |
| 4,373,517 A * | 2/1983 | Criscuolo ............. A61F 5/3753 602/20 |
| 4,417,569 A | 11/1983 | Brudny |
| 4,598,703 A | 7/1986 | Lindemann |
| 4,716,895 A | 1/1988 | Marques et al. |
| 4,751,923 A | 6/1988 | Marino |
| 4,834,082 A | 5/1989 | Ghadiali |
| 5,033,461 A * | 7/1991 | Young ................... A61F 5/3753 602/16 |
| 5,086,762 A | 2/1992 | Chee |
| 5,203,763 A | 4/1993 | Lajiness-O'Neill |
| 5,358,470 A | 10/1994 | Johnson |
| 5,358,471 A | 10/1994 | Klotz |

(Continued)

FOREIGN PATENT DOCUMENTS

| | | |
|---|---|---|
| DE | 3936232 | 5/1991 |
| EP | 0198482 | 4/1986 |
| WO | WO 2009/076725 | 6/2009 |

OTHER PUBLICATIONS

U.S. Appl. No. 14/253,343, filed Apr. 15, 2014, Krenzel.

(Continued)

*Primary Examiner* — Tarla Patel
(74) *Attorney, Agent, or Firm* — Sheridan Ross P.C.

(57) ABSTRACT

A contouring arm and shoulder support is provided that is secured to a supporting and stabilizing belt. The support system comprises a belt support and an arm support that are operatively interconnected and yet easily disassociated. The arm support provides dynamic support that allows the patient to move their injured arm if needed.

23 Claims, 23 Drawing Sheets

(56) References Cited

U.S. PATENT DOCUMENTS

| | | | |
|---|---|---|---|
| 5,385,536 A * | 1/1995 | Burkhead | A61F 5/3753 2/45 |
| 5,403,268 A | 4/1995 | Clement | |
| 5,407,420 A * | 4/1995 | Bastyr | A61F 5/05858 602/16 |
| 5,520,620 A | 5/1996 | Johnson | |
| 5,538,499 A * | 7/1996 | Schwenn | A61F 5/3753 602/16 |
| 5,558,626 A | 9/1996 | Holtzman et al. | |
| 5,628,725 A | 5/1997 | Ostergard | |
| 5,682,653 A | 11/1997 | Berglof et al. | |
| 5,857,990 A | 1/1999 | Maas | |
| 5,867,826 A | 2/1999 | Wilkinson | |
| 6,045,520 A * | 4/2000 | Buckley | A61F 5/05858 602/16 |
| 6,099,489 A | 8/2000 | Herzberg et al. | |
| 6,106,493 A | 8/2000 | Rozell | |
| RE36,869 E | 9/2000 | Ewen | |
| 6,292,985 B1 | 9/2001 | Grunberger | |
| 6,421,834 B2 | 7/2002 | Kester | |
| 6,464,656 B1 | 10/2002 | Salvucci et al. | |
| 6,837,862 B2 | 1/2005 | Driver | |
| 6,945,945 B2 | 9/2005 | Givler et al. | |
| 6,979,303 B2 | 12/2005 | Jestrabek-Hart | |
| 7,789,114 B2 | 9/2010 | Pace et al. | |
| 8,109,273 B2 | 2/2012 | Golden et al. | |
| 8,196,588 B1 | 6/2012 | Krenzel | |
| 8,763,209 B2 | 7/2014 | Kavarsky et al. | |
| 9,044,324 B2 | 6/2015 | Krenzel | |
| 2005/0273026 A1 | 12/2005 | Howard | |
| 2007/0129657 A1 | 6/2007 | Fisher | |
| 2008/0108917 A1 | 5/2008 | Joutras et al. | |
| 2012/0101419 A1* | 4/2012 | Bonutti | A61F 5/013 602/20 |

OTHER PUBLICATIONS

"Arm Escort," Maddak Inc., 2000, retrieved from http://shop.maddack.com/p/art-escort-right-medium, 2 pages.
"ComfySplints," Lenjoy Medical Engineering, Inc., 2011, 28 pages.
"DonJoy Shoulder Cradle," DJO Global, 2014, [retrieved on Feb. 25, 2014], 3 pages. Retrieved from: www.djoglobal.com/products/donjoy/donjoy-shoulder-cradle.
"GivMohr® Sling," Patterson Medical Holdings, Inc., 2014, retrieved from http://www.pattersonmedical.com/app.aspx?cmd=getProduct&key=IF_921023482, 1 page.
"Lerman Shoulder," DJO Global, 2014, [retrieved on Feb. 25, 2014], 1 page Retrieved from: www.djoglobal.com/products/donjoy/lerman-shoulder.
"Loc-Line, The Original Modular Hose System," Lockwood Products, Inc., 2004, retrieved from http://www.commercservice.sk/images/katalog%20locline.pdf, 22 pages.
"Omo Neurexa," Otto Bock Scandinavia AB, 2008, retrieved from http://www.chemitec.co.il/images/stories/documents/shikum/omo_neurexa_leaflet_en.pdf, 8 pages.
"S.C.O.I. Shoulder Brace," DJO Global, 2014, 1 page.
Ambroise, The Wilmer® Carrying Orthosis; Wilmer® Carrying Orthosis for Brachial Plexus; www.ambroise-uk.com/carryingOrthosis.htm; Mar. 26, 2003; 1 page.
Arm Slings: Universal Shoulder Immobilizer—FastHealth Sports Injury Store; www.fasthealth.com/store/motion/ortho-12-4129.php; Apr. 4, 2003; 1 page.
Bird & Cronin, Inc.; 4 pages of various Slings, Shoulder Immobilizers; Therapy Wraps, etc.; 1-800-328-1095, date unknown.
BREG; Neutral Wedge; date unknown, 2 pages.
Dalco Arm Slings; www.dalcointernational.com/Dalco_Arm_Slings.html; Feb. 4, 2003; 2 pages.
Donjoy; UltraSling® ER; Introducing the Revolutionary UltraSling® External Rotation, date unknown, 1 page.
Frank Stubbs, Inc.; www.fstubbs.com/noflash/orthooedic/324.htm; Dec. 1, 2003; 1 page.
Joslin Orthopedic Gear; The Ultimate Arm Sling®; Arm Sling Design; www.armsling.com/design.htm; Feb. 8, 2003; 2 pages.
Manor Drug Store; www.manordrug.com/FLA/fla/products/28-911.htm; Dec. 1, 2003; 1 page.
Professional Products, Inc.; R000333 A/K; The Six Shooter; 2001, 1 page.
Royce Medical®; Orthopaedic Supplies; Arm Slings; Shoulder Immibilizers; Clavicle Supports, et al., date unknown, 1 page.
SupportsUSA, shoulder supports, arm slings and immobilizers; www.supoortsusa.com/arm/shoulder; Mar. 11, 2003; 3 pages.
SupportsUSA; Bicro™ Shoulder Immobilizer; http://supports4less.com/birdcronin/shouldersupports/bicroshoulderimmobilizer.htm; Feb. 4, 2003; 1 page.
SupportsUSA; Comfor™ Shoulder Immobilizer. Universal; http://supports4less.com/birdcronin/shouldersupports/comforuniversal•shoulderimmobilizer . . . ; Feb. 4, 2003; 1 page.
SupportsUSA; Sling and Swathe Shoulder Immobilizer; http://supports4less.com/birdcronin/shouldersupports/slingswatheshoulderimmobilizer.htm; Feb. 4, 2003; 1 page.
SupportsUSA; Super Sling—Universal Shoulder Immobilizer; http://supports4less.comfbirdcronin/shouldersupports/superslingshoulderimmobilizer.htm; Feb. 4, 2003; 1 page.
Therafin Corporation; www.therafin.com/armposition.htm; Feb. 27, 2004; 2 pages.
Official Action for U.S. Appl. No. 13/306,285 mailed Dec. 19, 2013, 12 pages.
Official Action for U.S. Appl. No. 13/306,285 mailed Jul. 7, 2014, 8 pages.
Notice of Allowance for U.S. Appl. No. 13/306,285 mailed Feb. 5, 2015, 9 pages.
Official Action for U.S. Appl. No. 14/253,343 mailed Oct. 27, 2015, 19 pages.
Final Official Action for U.S. Appl. No. 14/253,343 mailed Mar. 10, 2016, 12 pages.
Final Action for U.S. Appl. No. 14/253,343 mailed Feb. 9, 2017, 15 pages.

* cited by examiner

SELECTIVELY ADJUSTABLE ARM AND SHOULDER SUPPORT

This application is a Continuation-In-Part of U.S. patent application Ser. No. 14/253,343, filed Apr. 15, 2014, the entire disclosure of which is incorporated by reference herein.

FIELD OF THE INVENTION

Embodiments of the present invention generally relate to an apparatus and method for supporting and selectively positioning a patient's arm. More specifically, the contemplated arm support maintains the patient's arm in such a way to prevent or reduce shoulder subluxation.

BACKGROUND OF THE INVENTION

Stroke and neurological injuries are difficult and costly to treat problems. Four out of every five American families will be impacted by stroke and four million Americans live with the lingering effects of a stroke, making stroke the leading cause of serious, long-term adult disability in the United States. Further, of the approximately 795,000 people who suffer stroke each year in the United States approximately 144,000 die, 185,000 are recurrent attacks, and 466,000 are new cases. An estimated 33% of stroke survivors need help caring for them and 70% cannot return to their previous occupations. According to research by the American Heart Association (AHA) and Centers for Disease Control (CDC), the estimated 2009 direct and indirect cost to cover inpatient care, rehabilitation, and follow-up care for lasting deficits of a stroke was $68.9 billion (numbers converted to 1999 dollars using the medical component of CPI). In 2010 the effects of a stroke alone are projected to cost the United States nearly $73.7 billion.

Given the number of affected persons and considerable cost for their care, much work has been done to identify clinical practices yielding the most satisfactory outcomes for glenohumeral subluxations (GHS), a common stroke after effect. Research has found that proactive, early intervention focused on supporting and stabilizing a patient's shoulder complex is critical for two reasons: 1) proper biomechanical positioning of the shoulder reduces secondary damage to the shoulder joint and capsule, and 2) proper shoulder support and positioning ameliorates pain. Clinical therapists report pain is a primary obstacle faced when implementing rehabilitative techniques for the upper extremity. Understandably, patients in pain are mentally distracted, unable to remain positive about their situations, and hindered in participating in recommended therapeutic regimes. Conquering pain becomes yet another task on the tortuous path to stroke recovery. Thus, tools that help ameliorate pain and maintain the integrity of the shoulder capsule are of critical importance to the occupational therapist.

Hemiplegic shoulder pain (HSP) and shoulder subluxation, i.e., a partial or complete dislocation, are common complications after a stroke or other neurological injury. Shoulder pain can begin as early as 2 weeks post stroke and results in significant long-term disability that impedes rehabilitation intervention, and limits the patient's ability to reach their maximum functional potential. Shoulder subluxations affect up to 81% of patients with hemiplegic shoulder pain and often occur during a "flaccid stage" of stroke recovery, i.e., wherein the patient suffers severe sensory loss rendering the patient's arm limp and floppy. Improper positioning of the shoulder and lack of support of the upper arm when in an upright position can contribute to subluxation, which aggravates shoulder pain and other secondary shoulder injury or stroke complications. For the majority of occupational therapists, proactively managing shoulder pain and implementing effective biomechanical joint positioning to compensate for lost muscle tone in the upper arm is critical to increase tolerance for other neuro-rehabilitative techniques and to maintain normal length of surrounding muscle/soft tissue. Most occupational therapists use supports, slings, straps, or functional electrical stimulation for the early intervention of GHS, but traditional apparatus are sometimes ineffective.

Several slings and arm support systems have been developed to help stabilize the shoulder complex. Examples include the Omo Nuerexa (Otto Bock®, Minneapolis Minn.), the GivMohr® Sling (GivMohr Corp., Albuquerque N. Mex.), and the Arm Escort (Maddak®, Wayne N.J.). Shoulder slings generally employ a cradle that receives the lower part of the arm. A strap is attached at one end of the cradle, is looped around the patient's neck and is attached to another end of the cradle to maintain the arm in a desired position. The length of the strap in a typical sling may be adjusted to allow the lower arm to be positioned within a certain angular range relative to the upper arm. Lengthening the strap increases the angle of the lower arm further relative to the patient's midsection, but the range of positions is limited by the sling structure.

While effective in some circumstances, slings and other similar devices have not been widely accepted for several reasons: 1) complicated strap arrangements make donning difficult, particularly for the elderly, those with cognitive deficits, and those who lack caregiver support; 2) the patient's arm is suspended at or just proximal to the hand which results in inadequate support while seated, a substantial portion of the patient's day; 3) large regions of the shoulder, arm, and hand are covered or encapsulated, which interferes with natural thermal regulation and makes the patient uncomfortable; and 4) pressure is applied across the patient's ipsilateral trapezius or contralateral axillary region, which causes additional pain, skin irritation and breakdown, or muscle pathologies. One of skill in the art will appreciate that slings can potentially exacerbate an injury by immobilizing the lower arm, and, thus preventing internal humeral rotation, which is ideal for protecting suture lines, but which also promotes anterior subluxations. Furthermore, existing sling designs only promote proper alignment of the upper arm when the entire arm should have support in the form of shoulder protraction, humeral external rotation with abduction and flexion, forearm supination, neutral wrist, extended fingers, and thumb abduction. To address the deficiencies of the prior art, therapists frequently fabricate less-than-ideal support systems from materials such as pillows, towels, and foam wedges. Further, patients often make do with slings that only partially support the arm in one position (sitting or standing).

Within the upper-limb rehabilitation field there exists a recognized need for new arm support options, particularly ones that are comfortable that are intuitive and easy to use, can be readily donned (preferably independently by the patient), can reduce pain, can promote proper entire arm alignment, are compatible with other treatment interventions, and offer greater dynamic support when sitting, standing and ambulating. The following disclosure describes an improved support that maintains the patient's arm in a predetermined position and that elevates the head of the patient's humorous into the shoulder socket to reduce pain and secondary damage. The contemplated support also addresses the issues outlined above and other issues understood by those of skill in the art.

SUMMARY OF THE INVENTION

It is one aspect of the present invention to provide an arm and shoulder support that maintains a patient's arm in a predetermined position and that prevents or reduces shoulder subluxation. The contemplated apparatus at least partially cradles the patient's arm and maintains it in a stable orientation. Thus, it is one aspect of embodiments of the present invention to provide an arm and shoulder support for maintaining a patient's arm in a predetermined position. The support comprises various components that work in concert to urge the patient's humorous upwardly in a comfortable manner such that the humorous head is firmly seated within the shoulder socket. One embodiment of the present invention comprises an adjustable belt for positioning about the patient's waist and an arm cuff that interconnects to the patient's forearm below the elbow. The cuff is interconnected to the belt by a strap that spans from the cuff to an attachment anchor point of the belt. The strap may comprise various interlocking straps, one being a cushioned and selectively adjustable shoulder component that rests on the patient's shoulder in a comfortable manner. Further embodiments of the present invention comprise additional features for securing the patient's lower arm near the wrist and providing a grip member for the patient's hand.

The support suspends the arm at the elbow just distal to the olecranon using a structurally rigid open-cuff that prevents soft tissue damage. Attached distally to the cuff is an adaptable component that supports the forearm in supination and the wrist in a neutral alignment, allowing for variable tone and ideal distal arm positioning. A posterior assist band may also be included to help minimize internal humeral rotation for patients who have increased muscle tone. Because the contemplated shoulder support uses a different anchoring system than existing designs and provides suspension at the elbow as opposed to just the wrist/hand, it functions well for users forced to spend a significant time sitting because of other motor impairments. The support also allows for a more natural arm swing, which facilitates balance during ambulation and protects the upper arm in functional transfers to/from sitting.

Existing strap designs support the compromised arm using ipsilateral over-the-shoulder webbing/straps positioned across the chest or contralateral shoulder auxiliary region. The prior art arrangements do not comfortably provide a force reaction point needed to pull the humeral head posterior and superior as required for effective glenohumeral alignment. And, they are also uncomfortable for women because of breast(s) compression. To address these issues, the device of embodiments of the present invention employ an adjustable belt anchor that is easy to don and adjust, provides the necessary reaction point to counter anterior-inferior subluxations, and serves as a functional and comfortable gait belt. Moreover, it has been found that many stroke patients lack sufficient dexterity, strength, and bilateral coordination needed to secure common plastic belt fasteners used in existing medical products, but can fasten common motor vehicle seat belt latches. The fastening mechanisms used with one embodiment of the device are larger in size, are simple to operate, and permit one-handed use for closure and cinching, which is an added advantage being that individuals find their use intuitive. The anchoring belt may also incorporate a contoured inner structural stay that reduces belt migration up the patient's back while providing a solid, secure attachment point for the shoulder component. The shoulder support system has been developed to be comfortable for patients in wheelchairs or those who must remain seated for extended periods and serve as a gait belt for therapists/caregivers during functional mobility.

The belt of one embodiment of the present invention selectively receives the back strap and functions to hold the shoulder component. This aspect of embodiments of the present invention is unique as no other subluxation device integrates a belt to achieve uniform engagement around a patient's waist. More specifically, U.S. Pat. No. 6,945,945 to Givler et al. ("Givler") describes a system that comprises a shoulder strap and associated elbow piece and hand grip. Givler, however, does not disclose using a belt for providing consistent pressure to the upper portion of the shoulder strap. Conversely, Givler interconnects one end of the shoulder strap to the patient's other shoulder, which is not ideal. Some belts of embodiments of the present invention have a moldable metal stay that contours to the patient's body and to help prevent distortion from the force generated by the tension applied by the back strap. In one embodiment of the present invention, the belt is made of foam padding and may include a stay. The stay may be a formable, resiliently-deflectable aluminum member, wherein when the belt is positioned around the patient's waist it overlaps to create a compressive force against the patient that stabilizes the members that connect to the arm support.

It is yet another aspect of the present invention to provide a shoulder support for securing a patient's arm in a predetermined position wherein a shoulder strap is not used. More specifically, in one embodiment of the present invention, the patient's arm is supported by supports, cuffs, and brackets that are interconnected to a plate secured on or about the patient's hip by way of an adjustable belt. Thus, the contemplated support fixes the patient's arm in a cantilevered fashion with respect to the patient's torso and no further support, such as an over-the-shoulder strap or other harness, is needed. The contemplated series of supports and associated adjustable brackets of one embodiment of the present invention are operatively interconnected such that a variety of support configurations can be maintained. For example, the contemplated support allows a caregiver to place and maintain the patient's arm in a predetermined orientation. Alternatively, the caregiver can maintain the position of a portion of the patient's arm and while allowing other portions, such as the wrist, to be moved. Thus, the contemplated arm support allows for the caregiver to limit certain degrees of freedom while freeing other degrees of freedom.

One embodiment of the present invention that does not rely on a shoulder strap utilizes a belt support. The belt support receives a corresponding arm support that receives the patient's arm. Alternatively, the belt support may selectively receive a cuff as described herein. The arm support is rotatably positioned within the belt support which allows the patient's forearm to rotate towards and away from their midsection, i.e., movement of the patient's hand adjacent to the stomach, pointing outwardly from the body, and laterally away from the body. In addition, the belt support and interconnected arm support of some embodiments can move upwardly and downwardly to suit the patient's physical characteristics and the caregiver's desires. Still further, embodiments of the belt support may be selectively tilted which moves the interconnected arm support accordingly to raise or lower the patient's hand. The caregiver can also position the arm in a natural position that does not affect walking. The arm position provided by this embodiment also prevents shoulder roll detrimental to proper rehabilitation.

The adjustability of the belt support and the rotatable interaction between the belt support in the arm support allows the caregiver to dynamically position the patient's arm. More specifically, the caregiver using the contemplated support system can position the patient's upper arm in such a way to address subluxation, rotate the forearm as desired, and position the hand, while allowing the patient to move their arm within a specific range. The patient or caregiver also has the ability to quickly and easily remove the arm from the support if needed or desired. One of skill in the art will appreciate that the apparatus and methods thus provide support with a degree of mobility which facilitates rehabilitation. The support system thus supports a portion of an injured patient's body while allowing the unaffected areas to move.

It is important to note that some embodiments the present invention do not employ a static interconnection between the belt support in the arm support. For that reason, the patient or caregiver can quickly and easily disassociate the arm support from the belt support. In operation, the patient will use their functioning arm and hand to slide the injured arm rearwardly to disassociate the arm support for the belt support. This feature allows patients to sit, which is especially desirable to patients confined to wheelchairs. This aspect also allows the patient to keep portions of the support system on (i.e., the belt support or the arm support) so that the injured arm can be quickly and easily reconnected before or just after standing.

It is another aspect of embodiments of the present invention to provide a selectively deflectable and positionable forearm and hand support. This aspect of the present invention allows the caregiver to selectively configure the arm support to accommodate a patient's arm shape and size. The ability to selectively configure the arm support also allows the caregiver to customize treatment to address how the stroke or other injury has uniquely affected the particular patient. One of skill in the art will appreciate it is desirable to allow the caregiver selectively form and shape the forearm or hand support to enhance patient comfort and to place the patient's arm in an orientation that facilitates rehabilitation. The contemplated arm support employs a moldable or selectively deflectable core member that is overwrapped with fabric and/or cushioning. Once the desired form is achieved, it will remain shaped. The selectively deflectable nature of the core member renders the arm support flexible yet stiff such that after customizing, it reacts loads generated by the patient's hand, often caused by "tone." The core member of one embodiment of the present invention is made of aluminum expanded metal. Thus, one embodiment of the present invention is a method of treating more than one injury (i.e., relieves subluxation, cradles a flaccid arm, and selective positions a hand to address tone). Some embodiments employ a heat-activated thermoset that must be heated and formed.

Although the foregoing is concerned with treating those afflicted by stroke, one of skill in the art will appreciate that the devices, systems, and methods discussed herein may be used for other orthopedic applications. For example, embodiments of the present invention may be used to treat collar bone injuries, rotator cuff injuries, separated shoulders, etc.

The Summary of the Invention is neither intended nor should it be construed as representing the full extent and scope of the present invention. Moreover, references made herein to "the present invention" or aspects thereof should be understood to mean certain embodiments of the present invention and should not be construed as limiting all embodiments to a particular description. The present invention is set forth in various levels of detail in the Summary of the Invention and in the attached drawings and the Detailed Description of the Invention and no limitation as to the scope of the present invention is intended by either the inclusion or non-inclusion of elements, components, etc. in this Summary of the Invention. Additional aspects of the present invention will become more readily apparent from the Detail Description, particularly when taken with the drawings.

BRIEF DESCRIPTION OF THE DRAWINGS

The accompanying drawings, which are incorporated in and constitute a part of the specification, illustrate embodiments of the invention and with the general description of the invention given above and the detailed description of the drawings given below, explain the principles of these inventions.

Figure 1:
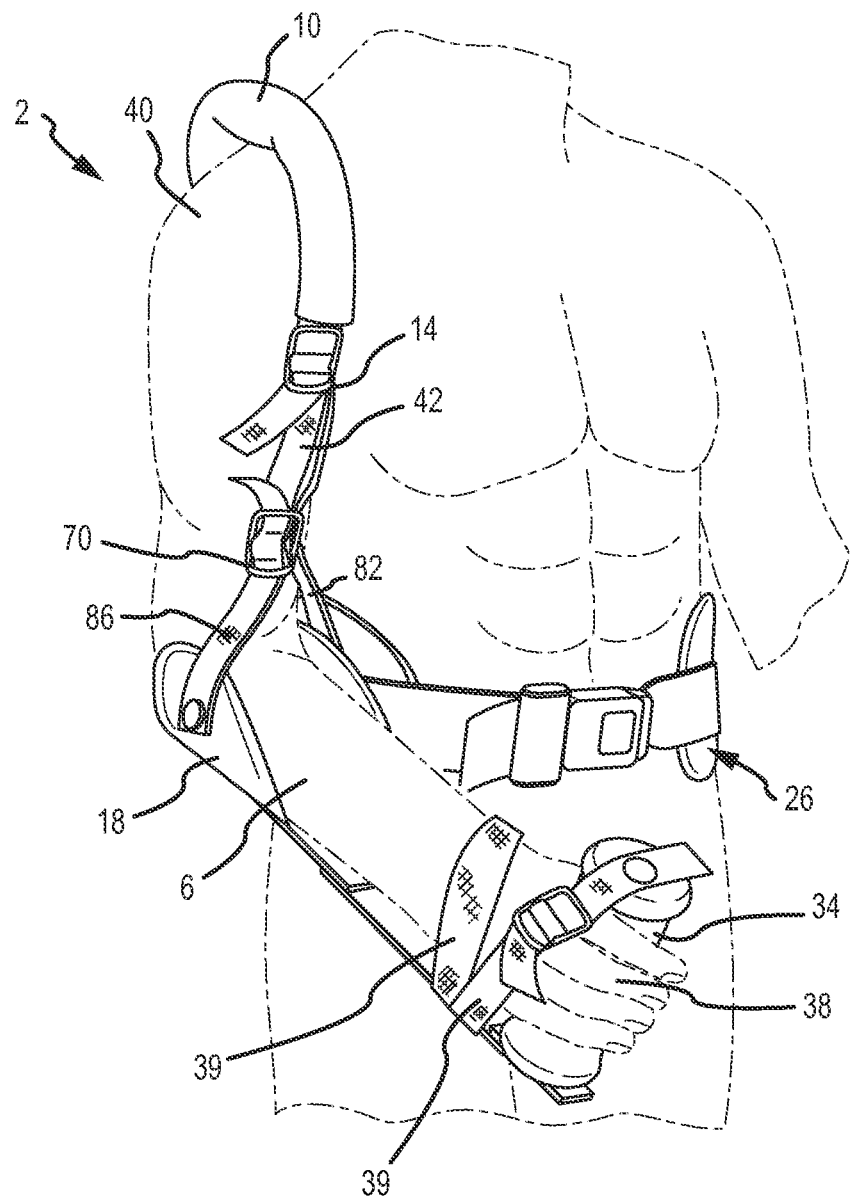
FIG. 1 is a front perspective view of a patient wearing a support of one embodiment of the present invention.

To assist in the understanding of one embodiment of the present invention, the following list of components and associated numbering found in the drawings is provided:

\# Component
2 Shoulder support
6 Arm
10 Shoulder component
14 First end
16 Adjustable strap
18 Arm cuff
22 Second end
26 Belt
26O Belt outer portion
26I Belt inner portion
34 Grip
38 Hand
39 Hand restraint
40 Shoulder
42 Front strap
46 Rear strap
54 Elbow
55 Fastening member
56 Hook material
57 Loop material
58 Core
59 Gap
62 Padding
\# Component
66 Cord
70 Ladder lock
74 Indentations
78 Lower arm
82 Medial strap
86 Lateral strap
90 First rigid member
94 Second rigid member
100 Primary belt
104 Padded belt
108 First end
112 Second end
114 Buckle
130 Grasp loop
202 Shoulder support
226 Belt
238 Hand
278 Forearm
300 Primary belt
304 Padded belt
316 End
318 Hip cushion
400 Belt support
404 Hip plate
408 Bar
412 Receiver
415 Fastener
417 Fastener
418 Top surface
419 Cavity
\# Component
420 Slot
424 Bearing surface
428 Wall
500 Arm support
518 Forearm portion
534 Hand portion
538 Strap
539 Strap
550 Post
552 Lower portion
560 Lower surface
600 Arm support
604 Hip plate
608 Bar
610 Belt support
612 Receiver
614 Forearm portion
615 Fastener
617 Fastener
618 Hip cushion
619 Cavity
620 Slot
624 Bearing surface
626 Belt
628 Wall
634 Hand portion
638 Strap
639 Strap
650 Post
652 Lower portion
\# Component
660 Lower Surface
664 Top surface
668 Lower surface
670 Plate
674 Slot
678 Head
682 Upper surface
686 Bottom portion
690 Inner surface
694 Top portion
698 Facet
700 Top surface
710 First belt portion
714 Back cushion
718 Top flap
722 Bottom flap
726 Zipper
730 Second belt portion
734 First belt portion rear end
738 Second belt portion rear end
742 Strap
746 Buckle
800 Locking mechanism
804 Ball
808 Arm
810 Screw
812 Indentation It should be understood the drawings are not necessarily to scale. In certain instances, details that are unnecessary for an understanding of the invention or that render other details difficult to perceive may have been omitted. It should be understood that the invention is not limited to the particular embodiments illustrated herein.

DETAILED DESCRIPTION

FIGS. 1-8 show an arm and shoulder support 2 for maintaining a patient's arm 6 in a predetermined position.

More specifically, one embodiment of the present invention generally comprises a shoulder component 10 that interconnects on a first end 14 to an arm cuff 18 and on a second end 22, adjacent to the patient's posterior, to an adjustable belt 26. The arm cuff 18 may be associated with a hand grip 34 that secures the patient's hand 38 with an adjustable restraint 39. The support 2 positions the patient's arm 6 such that the head of the humerus is transitioned upwardly into the shoulder socket 40, which reduces pain and facilitates rehabilitation and recovery.

An adjustable front strap 42 is used to interconnect the shoulder component 10 to the arm cuff. Similarly, an adjustable rear strap 46 is used to interconnect the shoulder component 10 to the belt 26. The straps allow the caregiver to customize the configuration of the support 2 to fit patient's need and body configuration. From an adjustable belt anchor point (see FIGS. 4 and 5) the rear strap 46 and shoulder component 10 traverse upwardly along the patient's back. The shoulder component 10 crosses the patient's ipsilateral scapula and is interconnected to the front strap 42, which is interconnected to the arm cuff 18 that secures the patient's arm 6 adjacent to the elbow 54.

Figure 3:
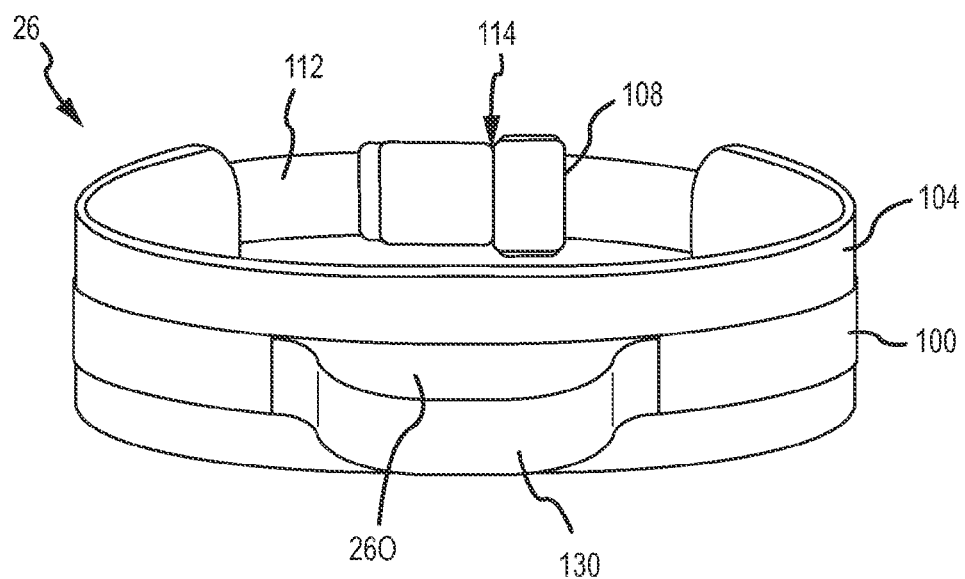
FIG. 3 is a rear perspective view showing a belt of one embodiment of the present invention.

FIG. 3 shows the belt of one embodiment of the present invention. The belt comprises a primary belt 100 of a first width interconnected to a padded belt 104 of a second width. The primary belt 100 is sewn or otherwise connected to the padded belt 104. In one alternative embodiment, however, of the present invention, the padded belt 104 is removable from the primary belt 100 to allow it to be cleaned or replaced. The primary belt 100 provides the support needed to secure the rear strap. The primary belt 100 has a first end 108 and a second end 112 associated with the conjoining parts of a buckle 114. In one embodiment, the buckle is similar to those commonly used for automobile seat belts, which facilitates interconnection by physically impaired individuals. The primary belt 100 is sewn or otherwise connected to the padded belt 104.

Figure 4:
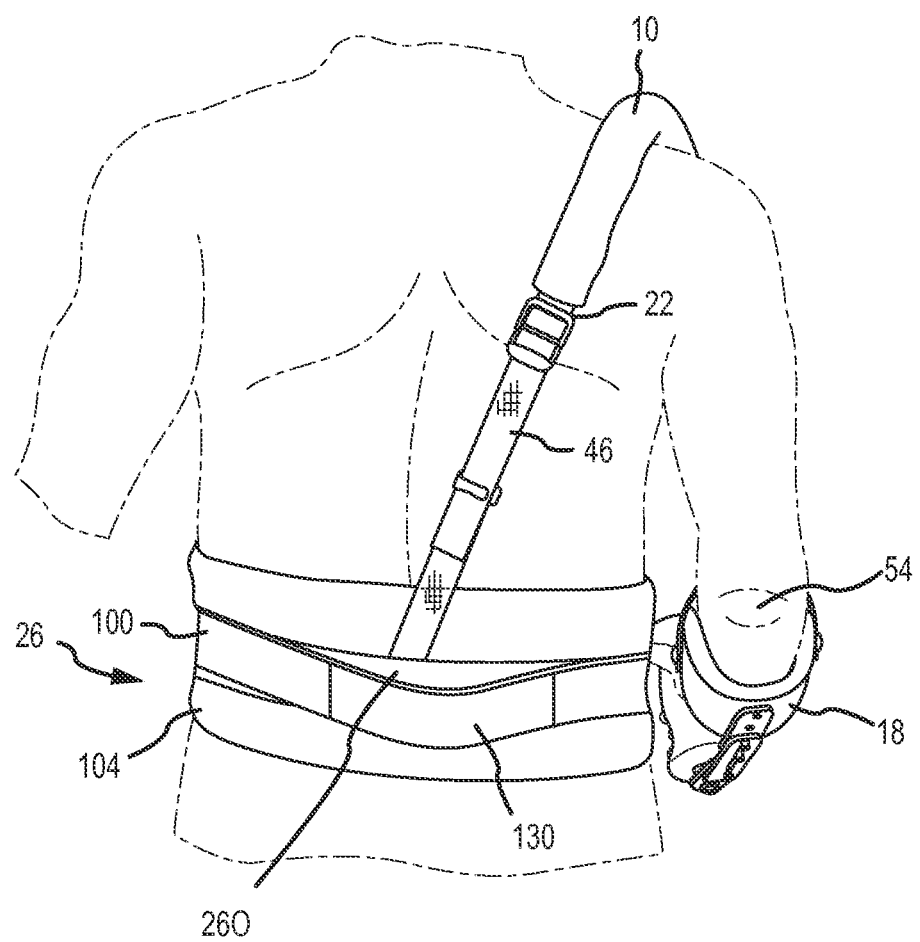
FIG. 4 is a rear elevation view of FIG. 1.
Figure 5:
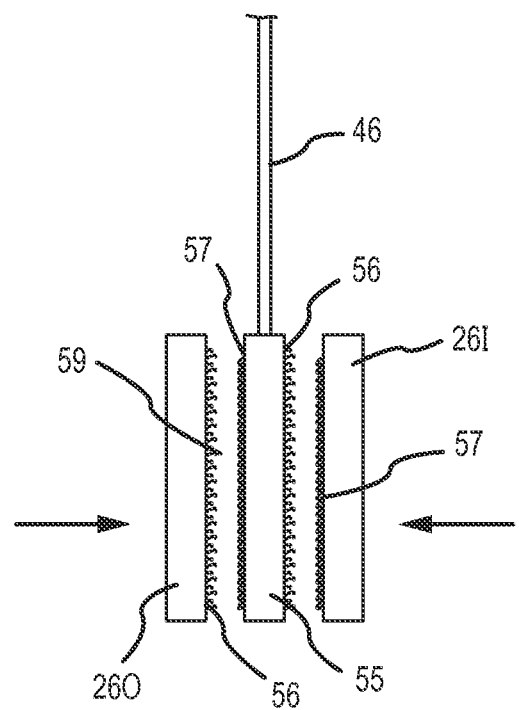
FIG. 5 is a cross-sectional view showing the interconnection between one end of a rear strap of the support and the belt.

Referring now to FIGS. 3-5, a method of interconnecting a rear strap 46 to the belt 26 is shown. More specifically, the rear strap 46 terminates in a fastening member 55 that has a selective interconnection mechanism on each side. For example, in one embodiment of the present invention, a hook and loop fastener is employed wherein one side of the fastening member is a hook material 56 and the other side is a loop 57 material. To adjust the angle and position of the rear strap 46, and thus the position of the shoulder component 10, an outer portion 26O of the belt is separated from an inner portion 26I of the belt. This provides a gap 59 for the receipt of the connecting member 55. In one embodiment of the present invention, the outer portion 26O of the belt includes a hook material 56 and the inner portion 26I of the belt includes a loop material 57. The connecting member 55 is placed within the gap 59 and the outer portion 26O of the belt and the inner portion 26I of the belt are brought together to capture the connecting member 55. In this way, the corresponding hook/loop surfaces of the connecting member 55, the outer belt member 26O, and the inner belt member 26I fix the position and angle of the rear strap 46. One of skill in the art will appreciate that the relative locations of the hook and loop material are not critical. Furthermore, other selective interconnecting mechanisms, such as magnets, snaps, etc. that are well known in the art may be employed instead of hook and loop fasteners. Further, the inner portion 26I of the belt may be a primary belt 100.

In another embodiment of the present invention the primary belt has a plurality of pockets each having a connector for receiving a complimentary connector on the end of the rear strap. Thus, the occupational therapist of the patient can selectively alter the angle that the strap and associated shoulder component is positioned on the patient's back. This additional functionality allows for the orientation of the strap and shoulder component to be modified depending on the patient's physical build, for example.

The primary belt 100 or padded belt 104 may also be associated with at least one grasp loop 130 (which may be the outer belt portion 26O). The grasp loop(s) 130 help the occupational therapist in lifting the patient to a standing position or placing them in a sitting position. Further, the grasp loop(s) 130 also help the caregiver guide and stabilize the patient has he or she is conducting therapy.

Figure 6:
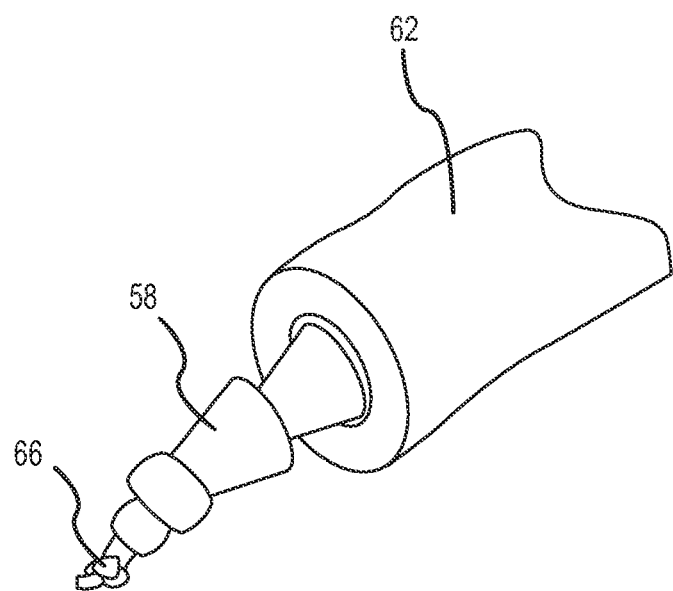
FIG. 6 is a partial perspective view of a shoulder component of one embodiment of the present invention.

Referring now to FIG. 6, instead of thin padded strapping or webbing found in traditional arm straps, one embodiment of the present invention employs an adjustable cushioned member with a core 58 that firmly holds its shape. For example, one embodiment employs Loc-Line® Modular Tube, made by Lockwood, Inc. that is covered with external padding 62 that supports the weight of the arm. By configuring (i.e. flexing) the adjustable core 58, patients can change the path of the shoulder component 10 over the affected shoulder and control the applied pressure. Contact locations on the shoulder can easily be adjusted by repositioning the core 58 whenever desired to shift the load for comfort or to avoid the patient's trapezius. Testing has shown patients particularly enjoy being able to easily move or flex the core 58 to avoid chafing, bruising, and excess contact pressure. This streamlined simplicity avoids complex harness schemes and is a significant advantage.

The shoulder component shown includes interlocking subcomponents 66 covered with padding 62 that are stiffened by compression. The shoulder component 10 is thus able to selectively bend and hold its position, thereby allowing the padded shoulder component 10 to contour to the patient's shoulder which increases comfort. In some embodiments of the present invention, the shoulder 10 component comprises a tension or bungee cord 66 for facilitating positioning and for providing additional flexibility. An adjustable ladder loc 70 (see FIG. 1, for example) is incorporated between the shoulder component 10 and front strap 42.

Figure 7:
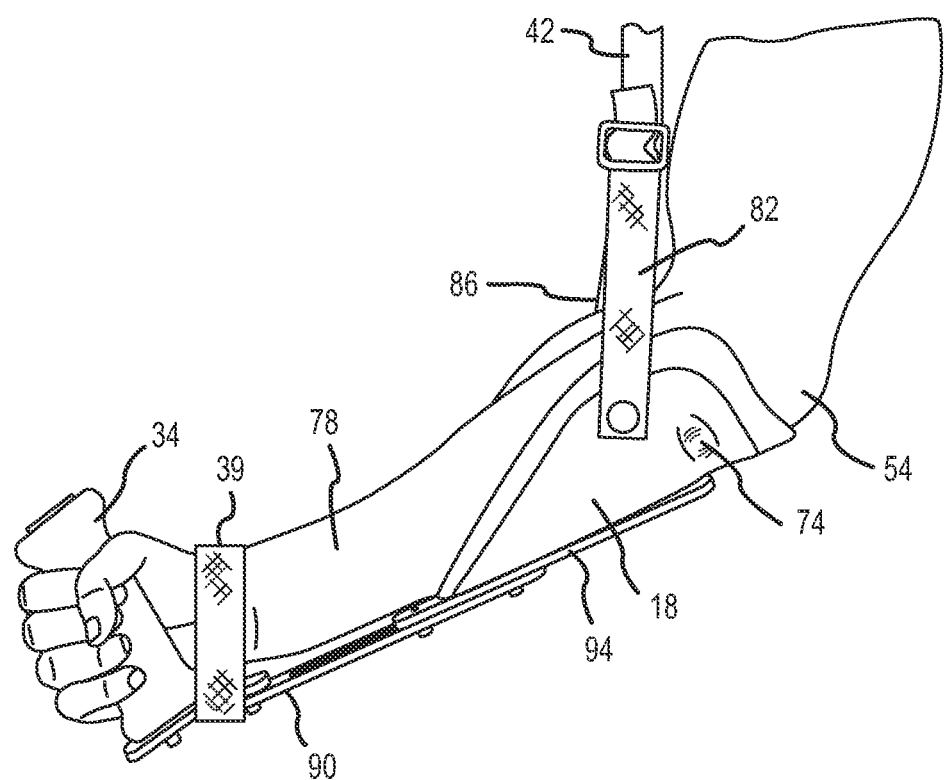
FIG. 7 is a side elevation view showing the patient's arm positioned in an arm cuff of one embodiment of the present invention.
Figure 8:
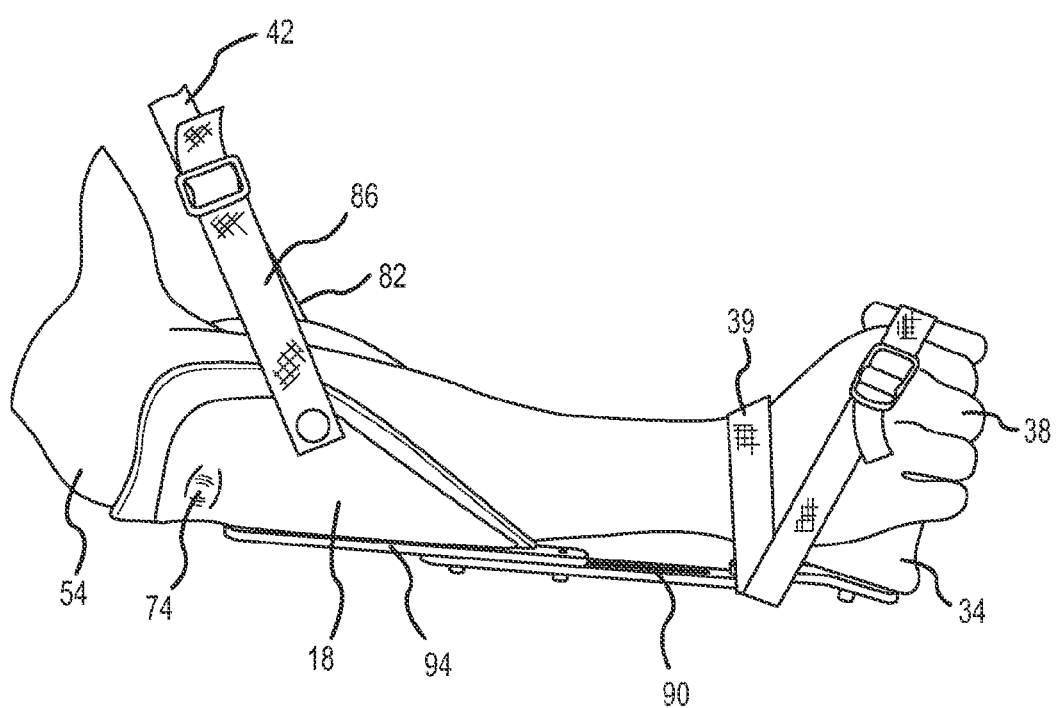
FIG. 8 is a side elevation view opposite to that of FIG. 7.

FIGS. 7 and 8 show a one-piece arm cuff 18 preferably molded from KYDEX brand ABS/vinyl sheet plastic. The arm cuff 18 supports the lower arm and helps lift the patient's upper arm into the shoulder joint. The arm cuff 18 may also include indentations 74 that firmly grasp the patient's lower arm 78. The front strap 42 includes a medial strap 82 and a lateral strap 86 that attach on either side of the arm cuff 18. The internal/external positions of the lower arm 78 can be altered by adjusting the length of the front strap 42 and/or the lengths of the lateral strap 86 and the medial strap 82. In one embodiment of the present invention, the arm cuff 18 uses snaps or hook and loop attachment members that receive the ends of the lateral strap 86 and the medial strap 82. The arm cuff may also include padding to provide comfort and adjustability required.

The grip 34 is attached to the arm cuff 18 and holds the patient's hand 38 in a specific position. The grip 34 is designed to arrest the patient's hand 38 and to give the patient something to grasp. In one embodiment, the grip 34 is interconnected to a first rigid member 90 interconnected to a second rigid member 94 attached to the arm cuff 18. The first rigid member 90 may be slidingly and/or rotatably interconnected to the second rigid member 94 so that the distance and/or relative angle between the grip 34 and the arm cuff 18 may be selectively altered. In this way, the caregiver can position the angle of the patient's wrist relative to their arm to increase or decrease wrist flexion. The grip 34 is preferably a tubular member that is over-molded with a soft foam material to accommodate various arm length and positions.

Figure 2:
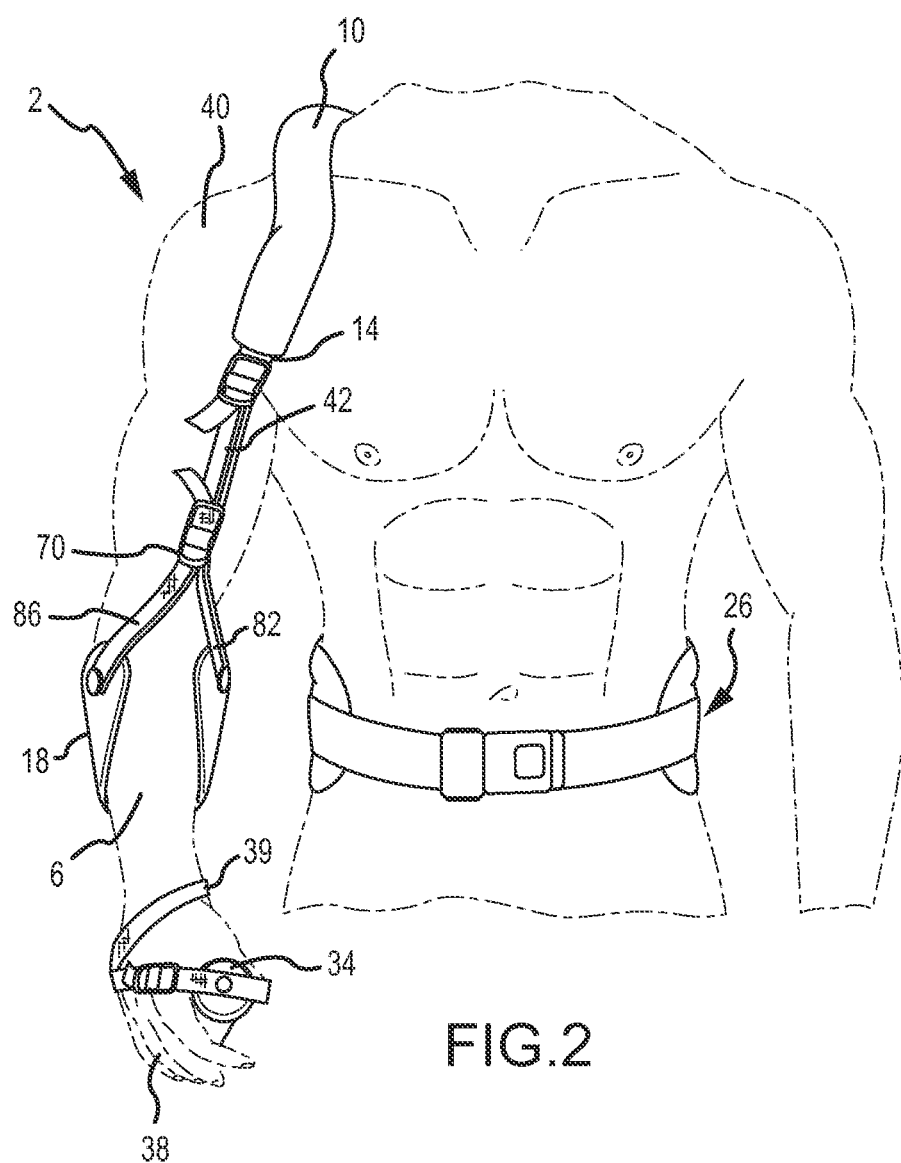
FIG. 2 is a front elevation view of FIG. 1.

FIGS. 9-15 show yet another embodiment of a shoulder support 202 that does not utilize the shoulder strap shown in FIGS. 1 and 2. A belt to 226 is employed which is similar to the belt employed by the embodiments described above. The belt 226 may include a primary belt 300 and a padded belt 304. The primary belt 300 may include a flexible metal stiffener. The incorporated metal support helps distribute load evenly around the patient's waist and to maintain desired arm pressure and orientation. An end 316 of the belt is selectively interconnected to the primary belt 300 by a hook and loop fastener, such as Velcro®. Alternatively, the belt ends may be interconnected with the buckle, such as the buckle device similar to that described above. The belt 226 may accommodate hip cushions 318 that enhances patient comfort. Although two hip cushions 318 are shown, one of skill in the art will appreciate that one hip cushion 318 may be employed without departing from the scope of the invention. The hip cushion 318 may be selectively removal removed which enhances adjustability and patient customization. Further, the belt 226 is associated with a belt support 400 that includes a hip plate 404, a movable bar 408, and receiver 412.

The patient interface associated with this embodiment of the present invention is an arm support 500 that includes a forearm portion 518 and the hand portion 534. The forearm portion 518 receives the patient's forearm, which may be secured to the forearm portion 518 by strap 538. Similarly, the patient's hand 238 may be secured to the hand portion 534 by at least one wrist strap 539. One of skill in the art will appreciate that the forearm portion 518 and hand portion 534 may be selectively interconnected and, thus, adjustable as shown in FIG. 7, for example, without departing from the scope of the invention. Also, the forearm portion 518 may be replaced by a customized cuff as described above. The arm support 500 also includes a post 550 extending from a lower surface thereof that is configured to selectively and operatively interconnect to the receiver 412 of the belt support 400. The post 550 of one embodiment of the present invention comprises a first end operatively interconnected to the arm support and a second end interconnected to a lower portion 552, wherein the first end and the second end define ends of a cylinder having a longitudinal axis. The lower portion 552 includes an upper surface spaced from a lower surface 560 to define a circular plate with an outer diameter greater than an outer diameter of the cylinder, wherein the circular plate is generally perpendicular to the longitudinal axis of the lower portion 552. In one embodiment, the post 550 is interconnected to the strap 538, which may be configured to selectively move along at least a portion of the length of the arm support 500. In an alternate embodiment, the post is rigidly interconnected to the arm support 500. Further, the arm support 500 may have a plurality of connection points that receive a removable post, which provides additional customization to the caregiver.

As mentioned above, the forearm portion 518 and the hand portion 534 may be selectively deformable and customizable. Alternatively, the forearm portion 518 may be made of a rigid material or a cuff, and the hand portion 534 can bend, mold, deform, or flex to accommodate the particular characteristics of a patient's hand or the caregiver's desires. In one embodiment, the hand portion 534 is larger than the patient's hand such that the hand portion 534 will substantially cradle the patient's hand. The hand support 534 may allow the patient's fingers to flexed upwardly or downwardly.

With particular reference to FIGS. 12-15, the bar 408 is selectively interconnected to the hip plate 40 and can move relative to the hip plate 404 along direction A. For example, it may be desirable to lower the patient's arm below the iliac crest, which will prevent the upper arm to be extremely biased upwardly. Once the desired bar 408 position is achieved, a fastener 415 is used to lock the bar 408 relative to the hip plate 404. The receiver 412 is operatively interconnected to the bar 408 and is able to rotate about axis B. A fastener 417 is used to fix the desired receiver orientation. In one embodiment, a top surface 418 of the receiver 412 is rotated downward (i.e., clockwise about axis B) about 20 degrees, which increases patient comfort. By setting the position of the bar 408 and the angle of the receiver 412, the caregivers is able to define a base arm support location.

After the bar 408 height and receiver 412 angle are set, they are fixed by their respective fasteners. Then, the post 550, which includes a lower portion 552 and a lower surface 560, is inserted within a cavity 419 of the receiver 412 wherein the lower portion 552 is positioned in a slot 420. The cavity 419 includes a bearing surface 424 that selectively engages the lower surface 560 of the posts 550. When inserted into the receiver 412, the post 550 is prevented from disengagement laterally along direction C, forward along direction D, and laterally along direction E. And interaction of a post top surface 564 and a wall 428 of the receiver 412 prevents disengagement in a direction parallel to axis F. The posts 550 in the receiver 412 are made of materials that allow for rotation of the post 550 about axis F. Other embodiments of the present invention utilize a magnetic interconnection that selectively fastens the post 550 to the receiver 412. Other embodiments use hook and loop fasteners to interconnect the post 550 to the receiver. Although the lower portion 552 is shown to be cylindrical, which allows for smooth rotation of the post 430 within the slot 420, one of skill in the art will appreciate that it can be faceted. More specifically, the lower portion 552 may have a square, pentagonal, hexagonal, etc. cross-section that allows the caregiver to selectively set the orientation of the arm support relative to the patient's body. That is, the caregiver may can incrementally set the angle of the forearm relative to direction D shown in FIG. 14. In some embodiments the lower portion 552 is removable where the caregiver can later use a cylindrical lower portion to allow relatively free rotation when the patient is ready.

Figure 9:
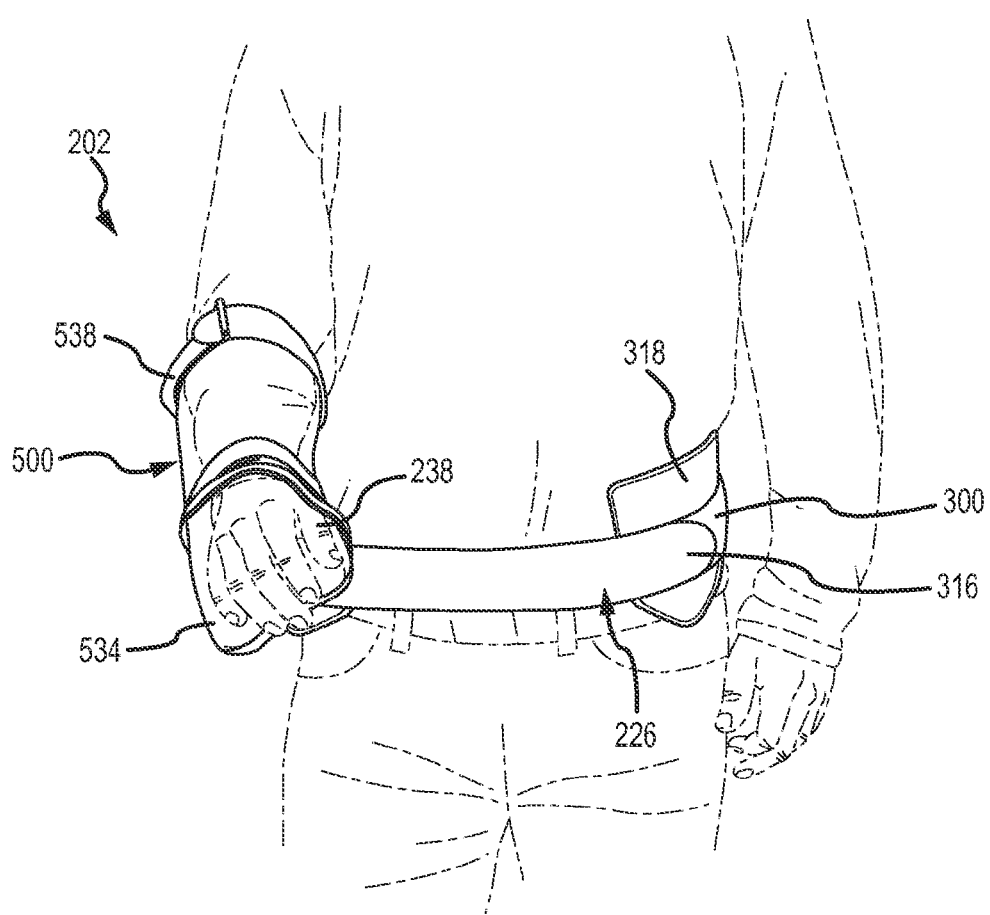
FIG. 9 is a front elevation view of another embodiment of the present invention that does not employ a shoulder strap.
Figure 10:
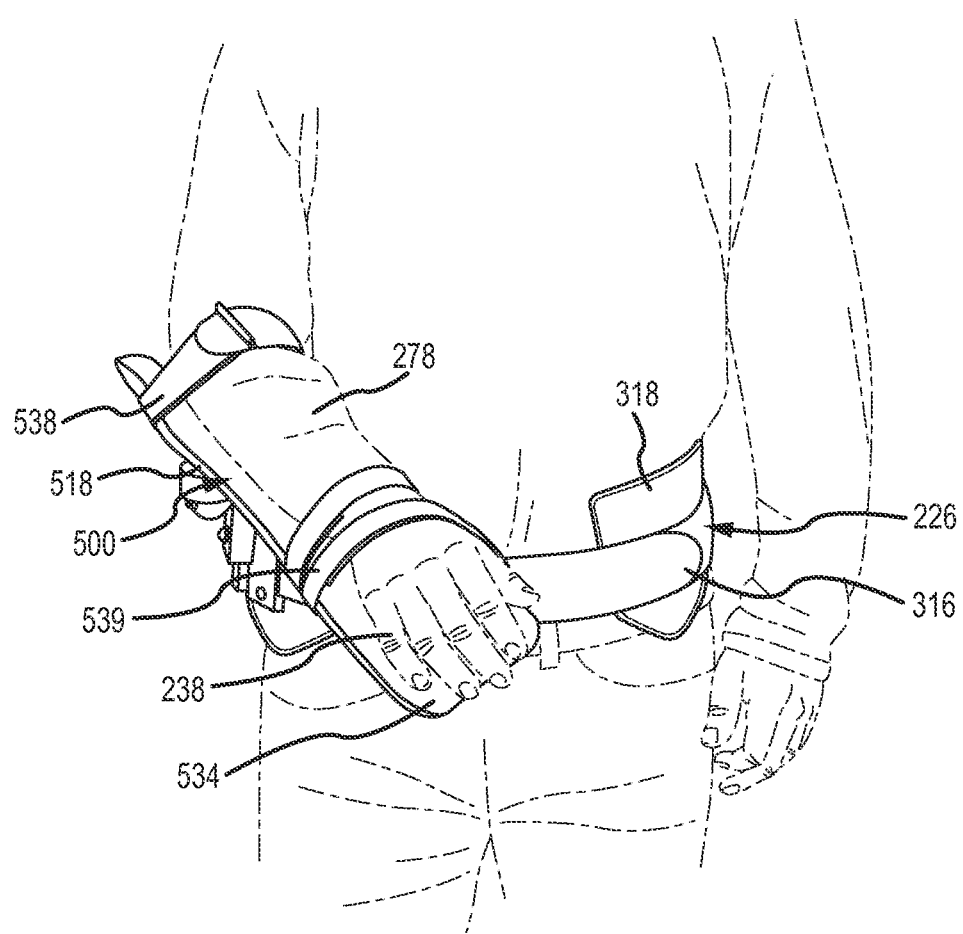
FIG. 10 is a front elevation view of the embodiment of FIG. 9 showing the patient's arm forearm rotated in front of their body.
Figure 11:
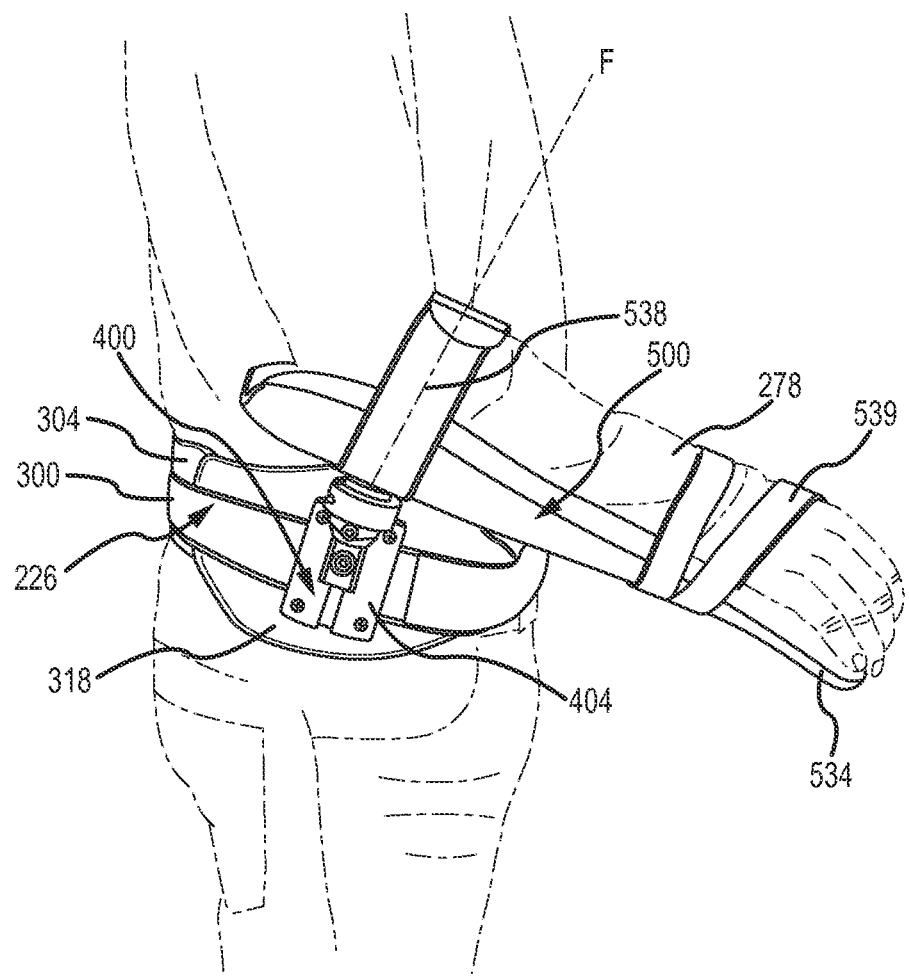
FIG. 11 is a side elevation view of the embodiment of FIG. 9.
Figure 12:
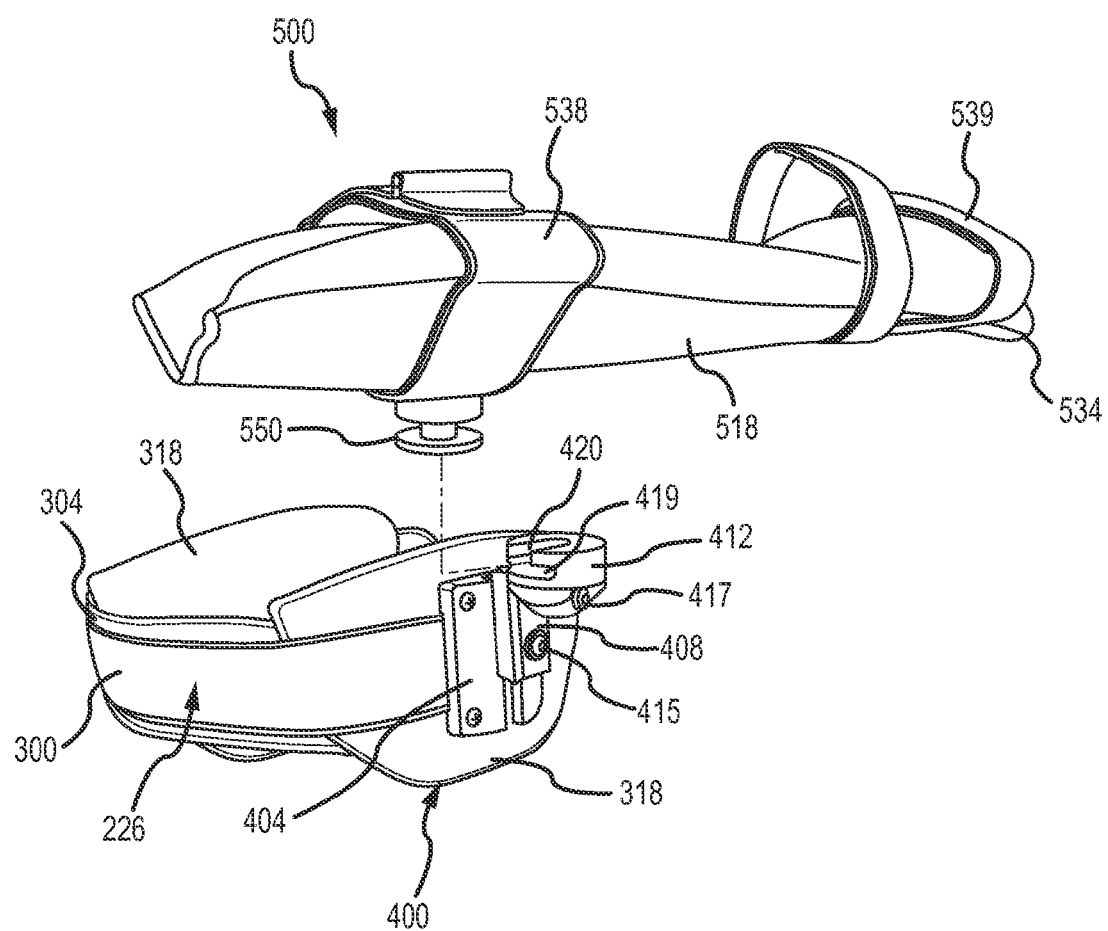
FIG. 12 is a rear perspective view of the embodiment of FIG. 9 showing an arm support disassociated from a belt support.
Figure 13:
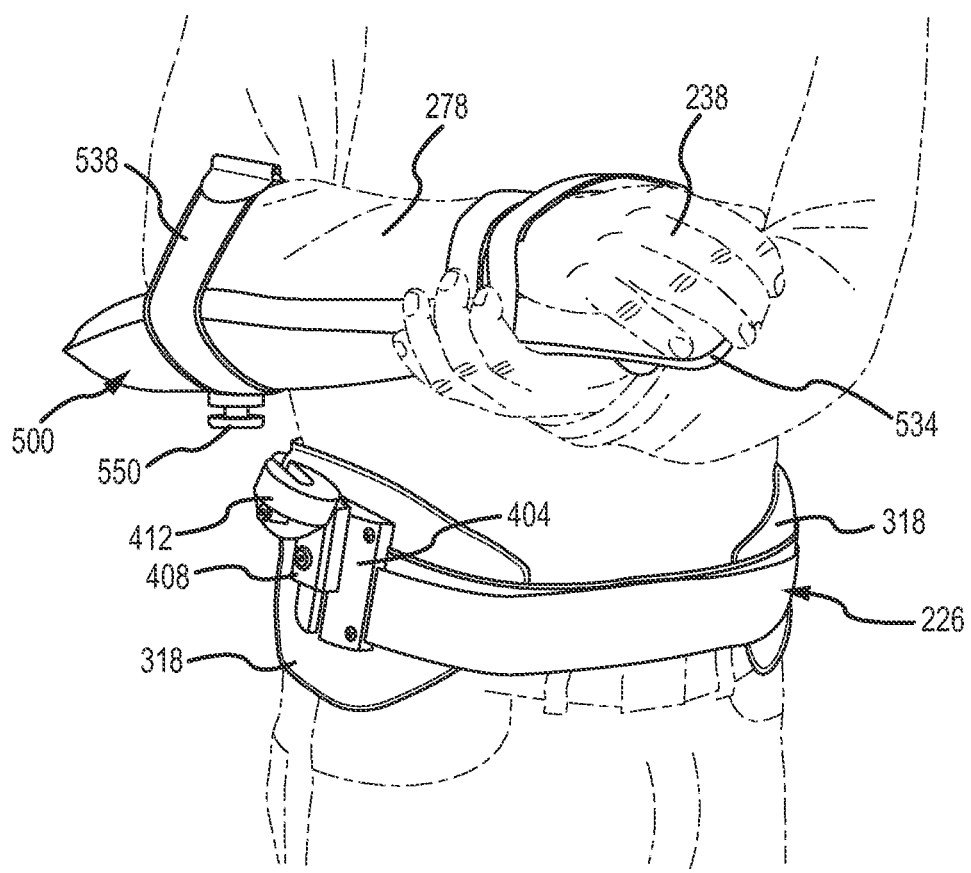
FIG. 13 is a perspective view of the embodiment of FIG. 9 wherein the arm support is disassociated from the belt support.
Figure 14:
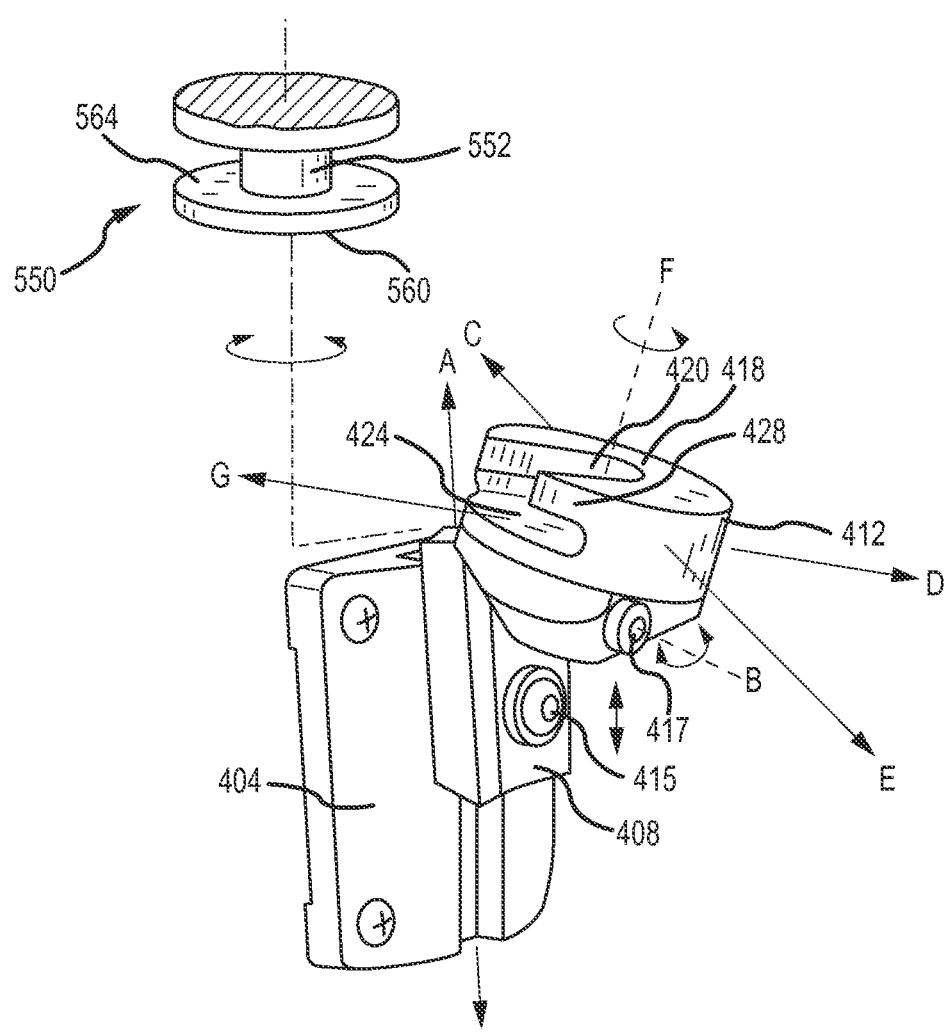
FIG. 14 is a detailed view of the embodiment shown in FIG. 9 wherein a post of the arm support is disassociated from the receiver of the belt support.
Figure 15:
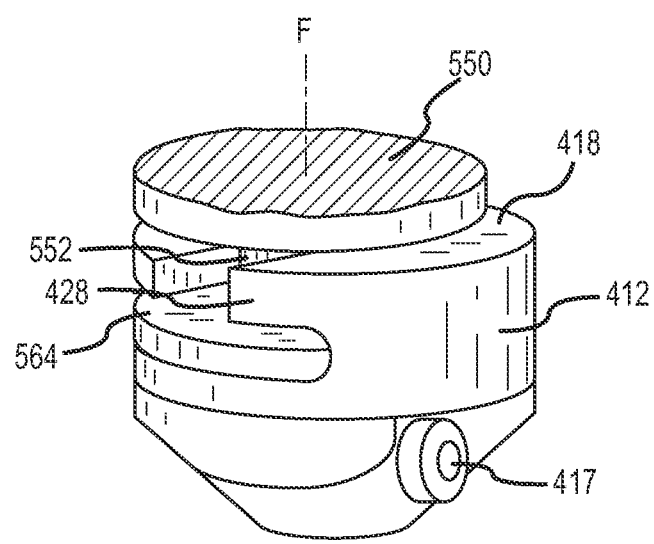
FIG. 15 is a detailed view of the embodiment shown in FIG. 9 wherein the post is associated with the receiver.
Figure 16:
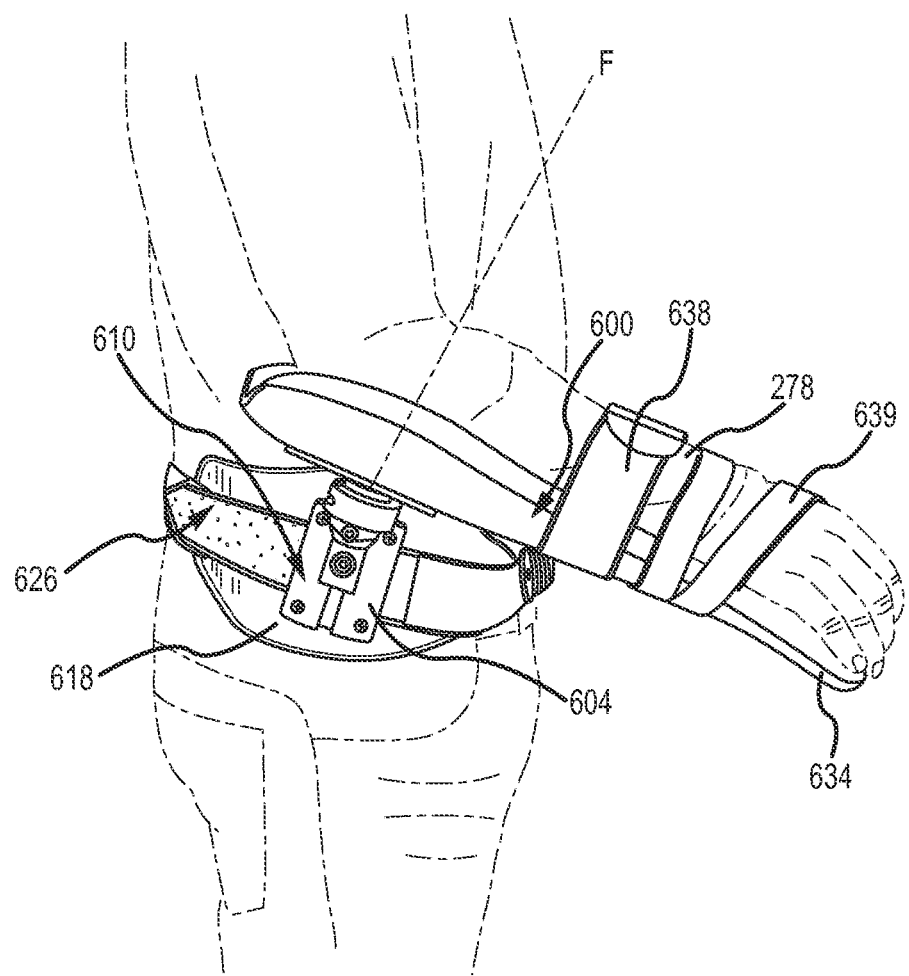
FIG. 16 is a side elevation view of an embodiment similar to that of FIG. 9.
Figure 17:
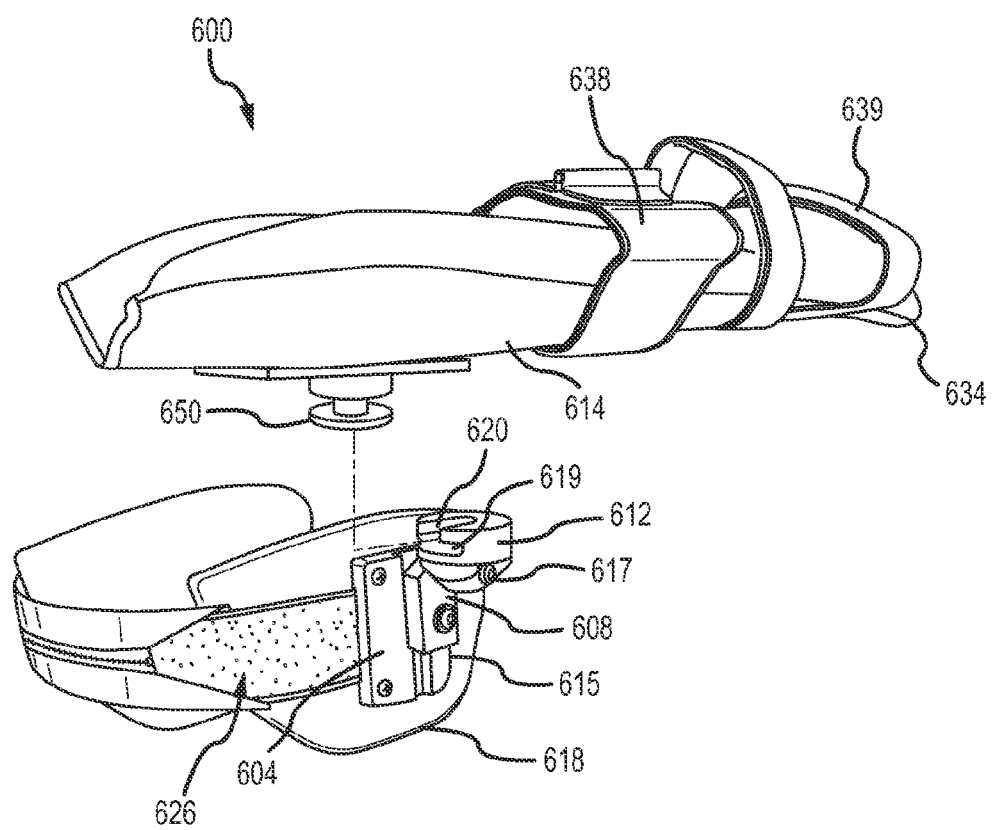
FIG. 17 is a rear perspective view of the embodiment of FIG. 16 showing an arm support disassociated from a belt support.

Referring to FIGS. 9-11, one of skill in the art will appreciate that the embodiments of the present invention allow for the caregiver to position the arm perpendicular to the patient as shown in FIG. 9 or angled slightly inwardly as shown in FIG. 10. The deformable forearm portion 518 or hand portion 534 also allows the caregiver to tilt the hand outwardly or position it flat depending on the needs of the patient. To remove the post 550 from the receiver 412, the caregiver or patient transitions the post rearwardly in direction G to guide the post 550 out of the cavity 419.

One of skill in the art will appreciate that the features of the embodiment shown in FIGS. 9-15 may be combined with those of FIGS. 1-8. For example, a strap 10 (FIG. 1) may be used in the embodiment of FIG. 9. The embodiment of FIG. 9 may also include a grip 34, without departing from the scope of the invention.

FIGS. 6-21 show yet another embodiment of a shoulder support that does not utilize the shoulder strap shown in FIGS. 1 and 2. The shoulder support includes belt ends that are interconnected with a buckle and strap commonly used with snow board bindings, which will be described below. The belt 626 accommodates hip cushions 618 that enhance patient comfort. Although two hip cushions 618 are shown, one of skill in the art will appreciate that one hip cushion 618 may be employed without departing from the scope of the invention. The hip cushion 618 may be selectively removed, which enhances adjustability and patient customization. Further, the belt 626 is associated with a belt support 610 that includes a hip plate 604, a movable bar 608, and a receiver 612.

Figure 19:
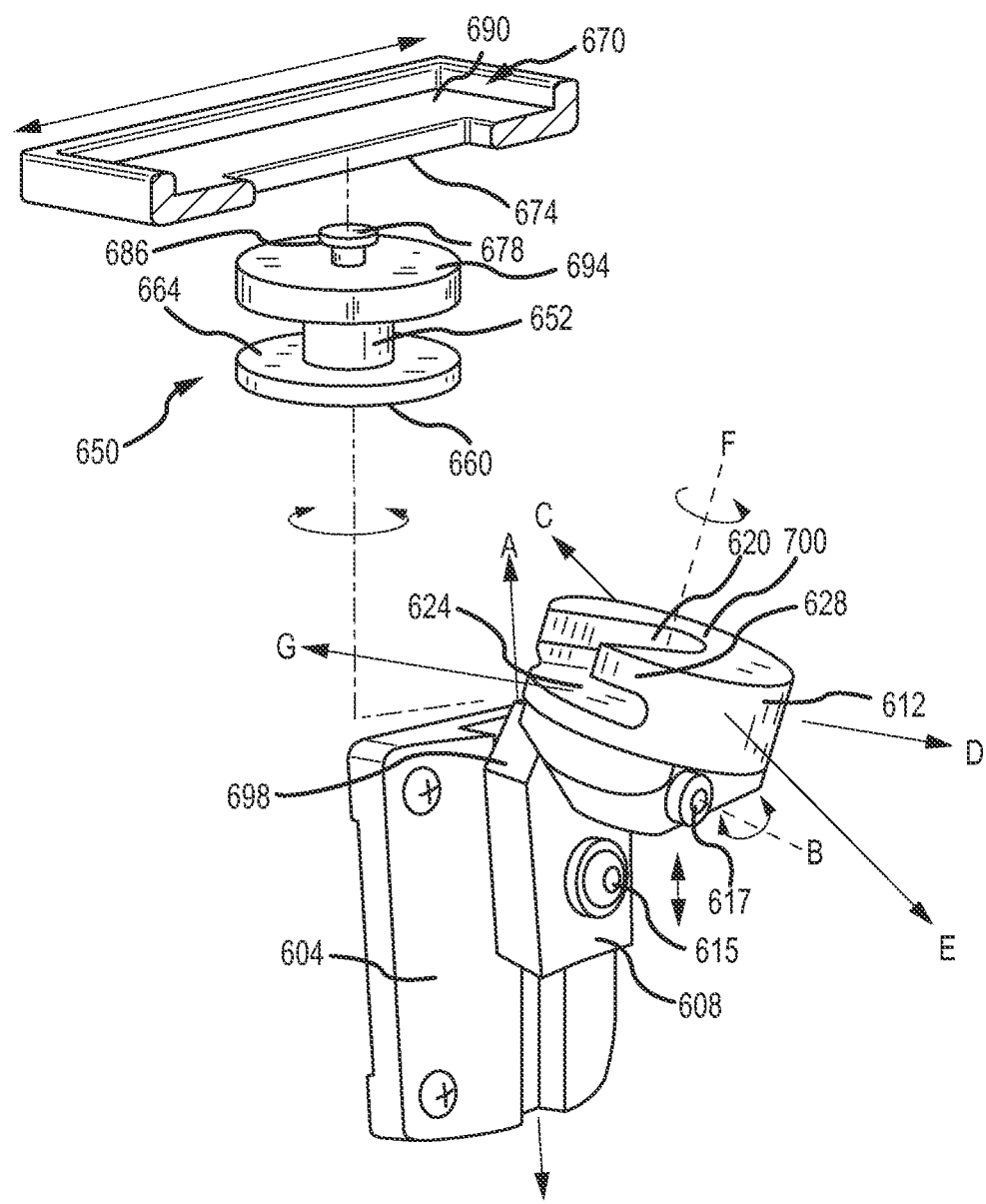
FIG. 19 is a detailed view of the embodiment shown in FIG. 16 wherein a post of the arm support is disassociated from the receiver of the belt support.

The patient interface associated with this embodiment of the present invention is an arm support 600 that includes a forearm portion 614 and the hand portion 634. The forearm portion 614 receives the patient's forearm 278, which may be secured to the forearm portion 614 by a strap 638. Similarly, the patient's hand 238 may be secured to the hand portion 634 by at least one wrist strap 639. One of ordinary skill in the art will appreciate that the forearm portion 614 and hand portion 634 may be selectively interconnected and, thus, adjustable as shown in FIG. 7, for example, without departing from the scope of the invention. Also, the forearm portion 614 may be replaced by a customized cuff as described above. The arm support 600 also includes a post 650 extending from a lower surface thereof that is configured to selectively and operatively interconnect to the receiver 612 of the belt support 610. Here, as shown in FIG. 19, for example, the post 550 may be slidingly interconnected to the forearm portion 614. More specifically, FIG. 19 shows a plate 670 that includes a slot 674 for receipt of a head 678 associated with the post 650. This provides a rigid yet selectively adjustable means for allowing the post 650 to move along the length of the forearm. The head 678 is associated with a hole (not shown) that extends through the post 650. A screw (not shown) is associated with a lower surface 668 of the posts interconnected to the post 650. In operation, once the position of the post relative to the plate 670 is identified, the screw is tightened, thereby moving the head 678 closer to an upper surface of the post 650, which engages a bottom portion 686 of the head 650 onto an inner surface 690 of the plate 670 and a top portion 694 of the post 650 against the plate 670.

As mentioned above, the forearm portion 614 and the hand portion 634 may be selectively deformable and customizable. Alternatively, the forearm portion 614 may be made of a rigid material or a cuff, and the hand portion 634 can bend, mold, deform, or flex to accommodate the particular characteristics of a patient's hand or the caregiver's desires. In one embodiment, the hand portion 634 is larger than the patient's hand such that the hand portion 634 will substantially cradle the patient's hand. The hand support 634 may allow the patient's fingers to flex upwardly or downwardly.

With particular reference to FIG. 19, the bar 608 is selectively interconnected to the hip plate 604 and can move relative to the hip plate 604 along direction A. For example, it may be desirable to lower the patient's arm below the iliac crest, which will prevent the upper arm to be extremely biased upwardly. Once the desired bar 608 position is achieved, a fastener 615 is used to lock the bar 608 relative to the hip plate 604. The receiver 612 is operatively interconnected to the bar 608 and can rotate about axis B. Excess rotation about axis B is prevented by faceted surfaces 698 on the bar 608. A fastener 617 is used to fix the desired receiver orientation. In one embodiment, a top surface 700 of the receiver 612 is rotated downward (i.e., clockwise about axis B) about 20 degrees, which increases patient comfort. By setting the position of the bar 608 and the angle of the receiver 612, the caregivers can define a base arm support location.

After the bar 608 height and receiver 612 angle are set, they are fixed by their respective fasteners. Then, the post 650 is inserted within a cavity 619 of the receiver 612 wherein the lower portion 652 is positioned in a slot 620. The cavity 619 includes a bearing surface 624 that selectively engages the lower surface 660 of the post 650. When inserted into the receiver 612, the post 650 is prevented from disengagement laterally along direction C, forward along direction D, and laterally along direction E. And interaction of a post top surface 664 and a wall 628 of the receiver 612 prevents disengagement in a direction parallel to axis F. The post 650 in the receiver 612 are made of materials that allow for rotation of the post 650 about axis F. Other embodiments of the present invention utilize a magnetic interconnection that selectively fastens the post 650 to the receiver 612. Other embodiments use hook and loop fasteners to interconnect the post 650 to the receiver. Although the lower portion 652 is shown to be cylindrical, which allows for smooth rotation of the post 650 within the slot 620, one of skill in the art will appreciate it can be faceted. More specifically, the lower portion 652 may have a square, pentagonal, hexagonal, etc. cross-section that allows the caregiver to selectively set the angulation of the arm support relative to the patient's body. That is, the caregiver may incrementally set the angle of the forearm relative to direction D shown in FIG. 19. In some embodiments the lower portion 652 is removable where the caregiver can later use a cylindrical lower portion to allow relatively free rotation when the patient is ready.

Figure 18:
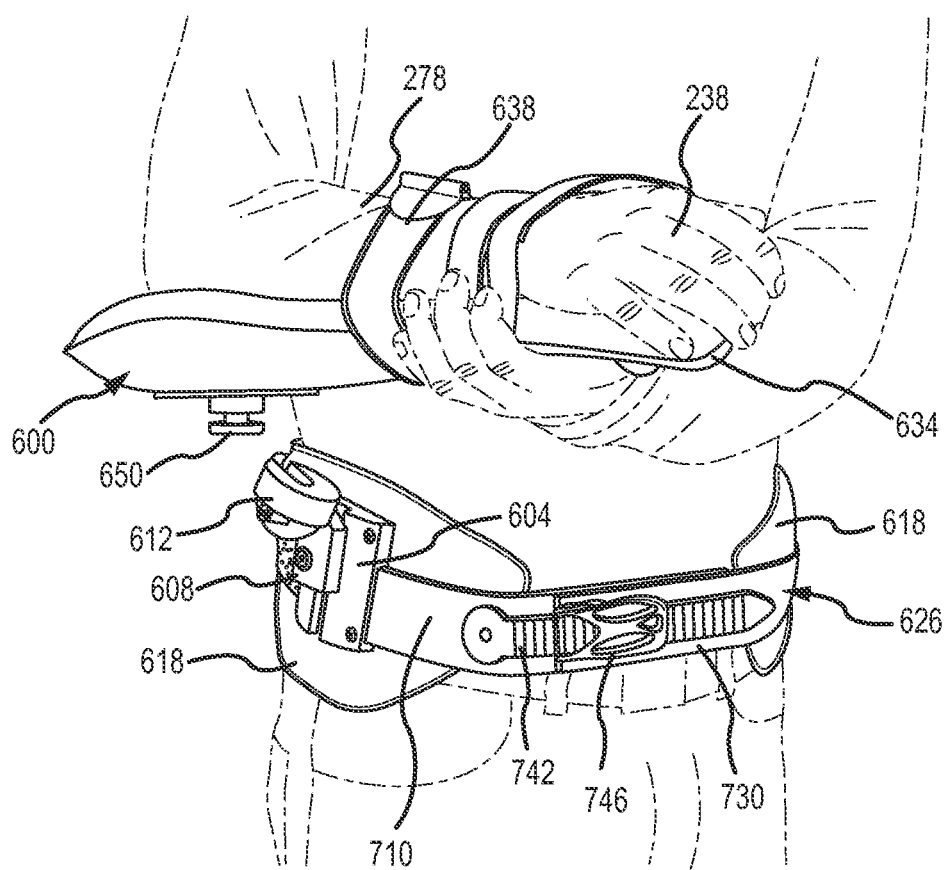
FIG. 18 is a perspective view of the embodiment of FIG. 16 wherein the arm support is disassociated from the belt support.
Figure 20:
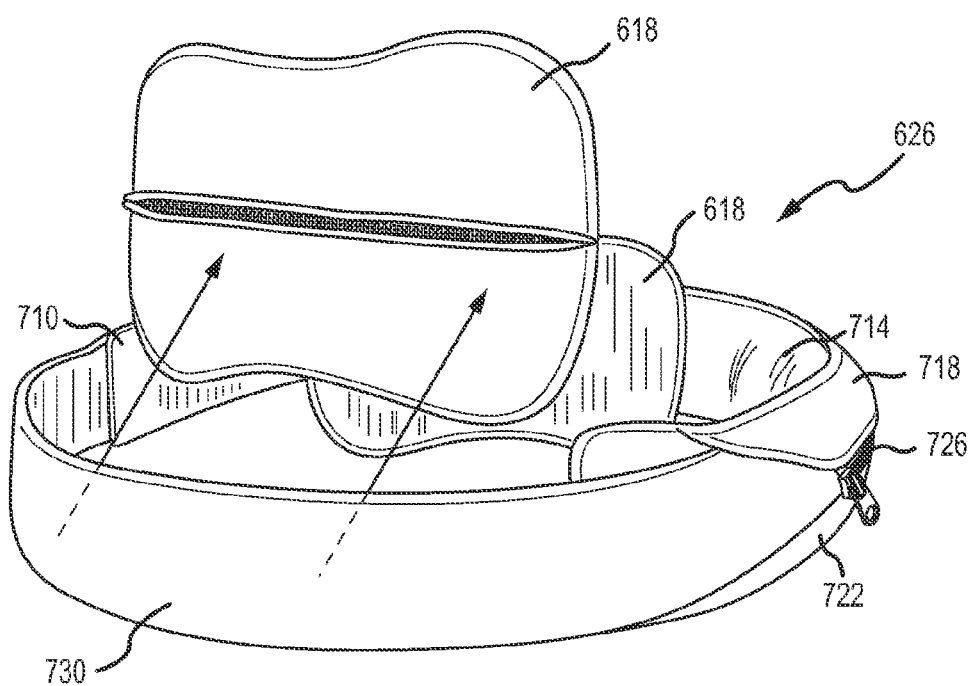
FIG. 20 is a rear perspective view of a belt used in the embodiment of FIG. 16.
Figure 21:
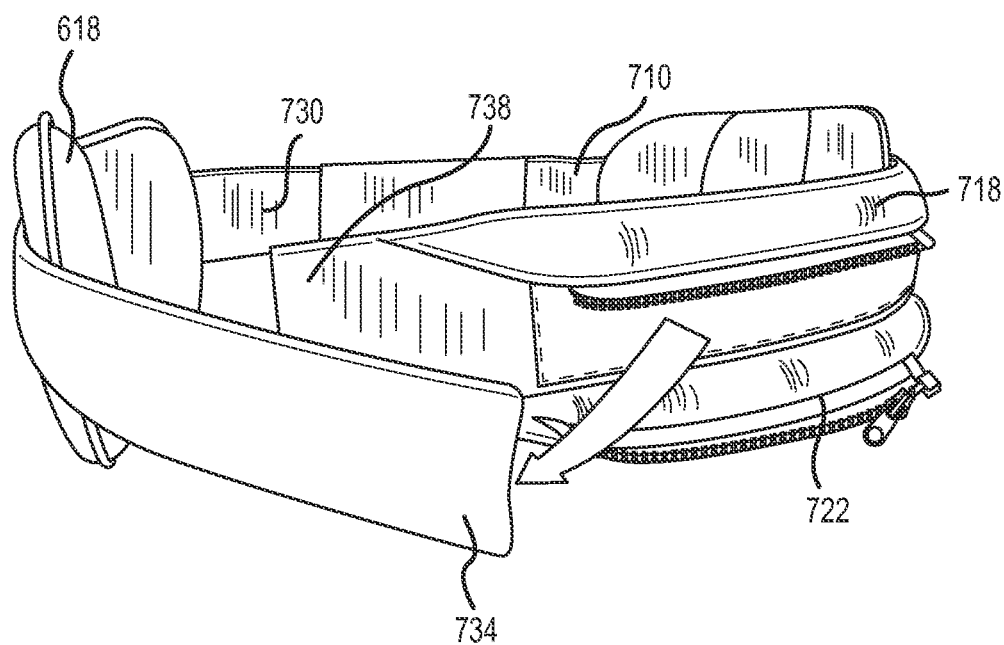
FIG. 21 is a rear perspective view of the belt of FIG. 16, wherein rear portions of a first belt portion and a second belt portion are disconnected.

FIGS. 18, 20, and 21 show the belt 626 of one embodiment of the present invention. The belt comprises a first belt portion 710 associated with a back cushion 714. The back cushion 714 includes a top flap 718 and a bottom flap 722 selectively interconnected by way of a zipper 726. One of ordinary skill in the art will appreciate that the top flap 718 and the bottom flap 722 may be selectively interconnected by other known methods, such as hook and loop fasteners. The first belt portion 710 accommodates a hip cushion 618. A second belt portion 730 includes a rear end 734 selectively interconnected to a rear end 738 of the first belt portion 710. In this example, the rear end 734 of the second belt portion is connected to the rear end 738 of the first belt portion 710 by way of a hook and loop fastener. Once interconnected, the top flap 718 and the bottom flap 722 are connected with the zipper 726, which maintains engagement of the belt portions' rear ends. The second belt portion 730 also accommodates a removable hip cushion 618. In operation, the size of the belt 626 can be selectively expanded or contracted by adjusting the overlap between the first belt portion 710 and the second belt portion 730. Once the desired size is achieved, the top flap 718 and the bottom flap 722 are connected.

FIG. 18 shows the front of the belt 626, which comprises a strap 742 associated with the first belt portion 710, and a buckle 746 associated with the second belt portion 730. The strap 742 and buckle 746 is very similar to that employed by snowboard bindings. The buckle 746 may allow for partial release such that the size of the belt may be quickly adjusted if needed. In operation, the rigidity of the strap 742 assists users, some of which are severely disabled, in inserting the strap 742 and into the buckle 746. After initial engagement, users can progress the strap 742 through the buckle 746 and then use the buckle 746 to incrementally tighten the belt 626. An example of a buckle and strap interconnection device that may be employed by some embodiments of the present invention is described in U.S. Pat. No. 8,763,209, which is incorporated by reference herein.

Figure 22:
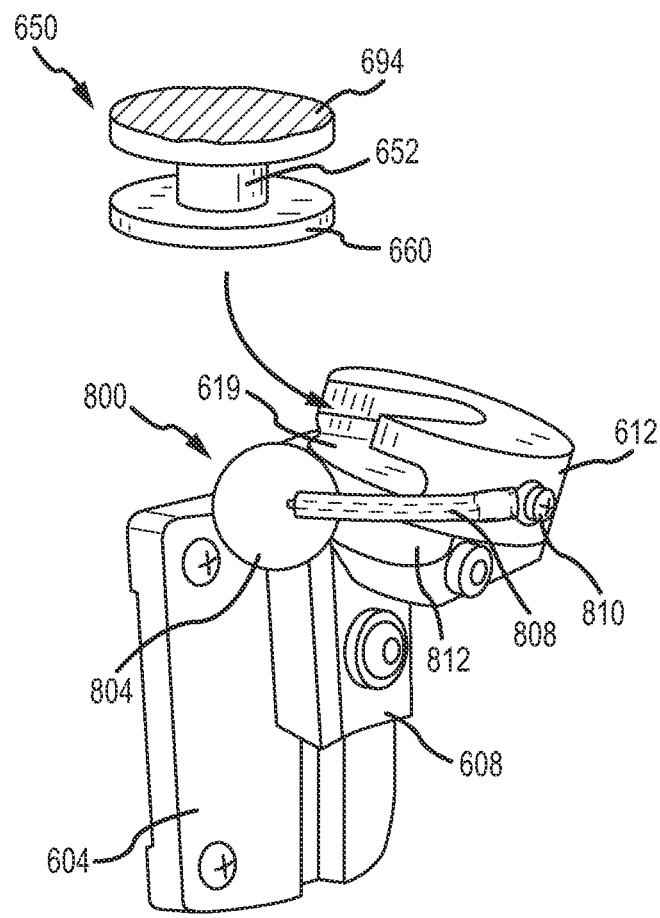
FIG. 22 is another embodiment of the present invention that employs a lock.
Figure 23:
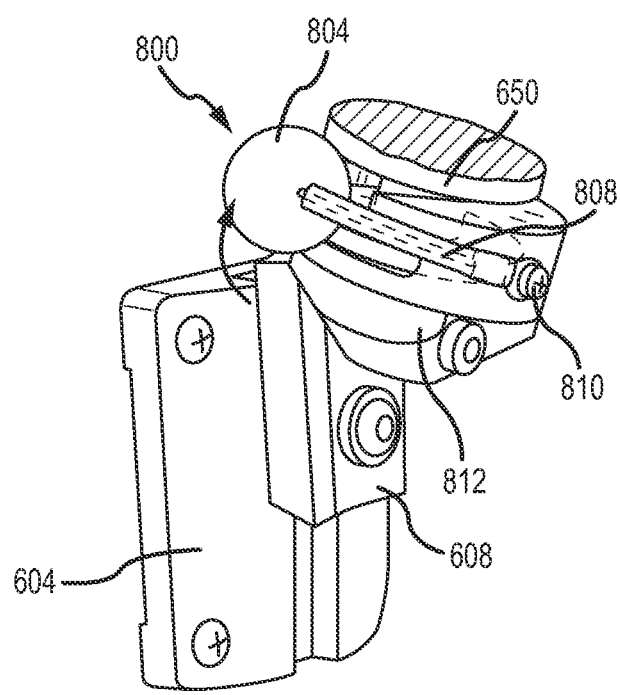
FIG. 23 shows the lock of FIG. 22 in a second position of use.

FIGS. 22 and 23 show one embodiment of the present invention that employs a locking mechanism 800. The locking mechanism 800 includes a ball 804 interconnected to the receiver 612 by at least one arm 808. Although a spherical locking portion is shown, one of ordinary skill in the art will appreciate that other shapes can be used without departing from the scope of the invention. The ball 804 is operatively interconnected to the receiver 612 by way of screws 810 and, thus, can selectively move to a first, open position of use to expose the cavity 619 such that the post 650 can be inserted into the receiver. The ball 804 may rest and an indentation 812 formed in the receiver 612, which helps maintain the ball 894 in the open position. Once the post 650 is placed within the receiver 612, the ball 804 is moved to the closed, locked position of use wherein the cavity 619 is blocked.

The arms 808 may be made of a resilient material, e.g., spring-like, wherein tension is applied by the arms 808 to the ball 804 so that the ball 804 is biased towards the receiver 612. The applied tension forces the ball 804 on to the receiver 612 and helps prevent post 650 removal. Although ball 804 and arms 808 are shown, one of ordinary skill in the art will appreciate other locking mechanisms may be used without departing from the scope of the invention. That is, any mechanism or device used to block the cavity 619, or to selectively prevent separation of the post 650 from the receiver 612, is contemplated.

One of skill in the art will appreciate that the features of the embodiment shown in FIGS. 16-23 may be combined with those of FIGS. 1-8. For example, a strap 10 (FIG. 1) may be used in the embodiment of FIG. 16. The embodiment of FIG. 16 may also include a grip 34, without departing from the scope of the invention. And all embodiments may employ a locking mechanism.

While various embodiments of the present invention have been described in detail, it is apparent that modifications and alterations of those embodiments will occur to those skilled in the art. However, it is to be expressly understood that such modifications and alterations are within the scope and spirit of the present invention, as set forth in the following claims. Further, the invention(s) described herein is capable of other embodiments and of being practiced or of being carried out in various ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

What is claimed is:

1. An arm support apparatus, comprising:
 a belt adapted to fit about a patient's waist;
 a support interconnected to said belt, said support comprising a means for selectively receiving;
 an arm support having a post extending therefrom, said post comprising a first end associated with said arm support and a second end interconnected to a lower portion, wherein said first end and said second end define ends of a cylinder having a longitudinal axis, wherein said lower portion includes an upper surface spaced from a lower surface to define a plate with an outer dimension greater than an outer diameter of said cylinder, wherein said post is selectively and operatively interconnected to said means for selectively receiving such that when interconnected said arm support is not statically interconnected to said means for selectively receiving and said post is able to rotate within said means for selectively receiving generally about said longitudinal axis of said cylinder; and
 a lock for maintaining the operative interconnection of said means for selectively receiving to said post of said arm support.

2. The apparatus of claim 1, wherein when said post is interconnected to said means for receiving, said post is capable of rotation, but not disassociation from said means for receiving, unless said post is moved in a predetermined manner.

3. The apparatus of claim 2, wherein when said means for receiving is a magnet or a hook and loop fastener.

4. The apparatus of claim 1, wherein when said means for selectively receiving is capable of moving and rotating.

5. The arm support apparatus of claim 1, wherein said support further comprises a hip plate, a movable bar, and receiver.

6. The apparatus of claim 5, wherein said bar is selectively interconnected to said hip plate and configured to move relative thereto, and wherein said means for selectively receiving is rotatably interconnected to said bar.

7. The apparatus of claim 1, wherein said means for selectively receiving includes a slot for receipt of said cylinder and a cavity for receipt of said lower portion, said cavity having a bearing surface that operatively engages said lower surface of said lower portion when said post is interconnected to said means for selectively receiving; and
 wherein said cavity is further defined by walls positioned about said slot that prevent disassociation of said post from said means for selectively receiving in a direction perpendicular to said bearing surface.

8. The apparatus of claim 1, wherein said arm support includes a forearm portion and a hand portion, wherein at least one of said arm portion and said hand portion is selectively deflectable, wherein at least one of said arm portion and said hand portion is able to assume a first position of use and a second position of use.

9. The apparatus of claim 1, wherein said arm support further includes an arm strap and a wrist strap.

10. The apparatus of claim 1, wherein said arm support is selectively positionable and made of a core comprised of bendable aluminum that is surrounded by a cushioning material.

11. The apparatus of claim 1, further comprising a forearm portion, said forearm portion being a trough-shaped arm cuff adapted to generally contour to a patient's lower arm, said arm cuff having an inner wall and an outer wall, wherein at least one of said inner wall and said outer wall includes an indentation that applies pressure to the patient's arm.

12. The apparatus of claim 1, wherein said belt is comprised of a first belt portion having a first end with a strap and a second end with a first means for interconnecting, and a second belt portion having a first end with a buckle for selective interconnection with said strap and a second end having a second means for interconnecting with said first means for interconnecting.

13. A method of treating a patient, comprising:
 providing an arm support apparatus, comprising:
 a belt adapted to fit about the waist of the patient;
 a support interconnected to said belt, said support comprising a means for selectively receiving; and
 an arm support adapted to receive the patient's arm, said arm support having a post extending therefrom, said post comprising a first end associated with said arm support and a second end interconnected to a lower portion, wherein said first end and said second end define ends of a cylinder having a longitudinal axis, wherein said lower portion includes an upper surface spaced from a lower surface to define a plate with an outer dimension greater than an outer diameter of said cylinder, wherein said post is selectively and operatively interconnected to said means for selectively receiving such that when interconnected said arm support is not statically interconnected to said means for selectively receiving and said post is able to rotate within said means for selectively receiving generally about said longitudinal axis of said cylinder;

placing said belt about the patient's waist;

placing the patient's arm within said arm support;

selectively interconnecting said post to said means for selectively receiving; and locking said post to said means for selectively receiving.

14. The method of claim 13, wherein the patient's arm can move adjacent to and away from the patient's torso when the arm support is not interconnected to said support interconnected to said belt.

15. The method of claim 13, wherein the patient's upper arm is firmly seated in the patient's shoulder socket.

16. The method of claim 13, wherein said method of treating a patient comprises at least one of relieving shoulder subluxation, cradling a flaccid arm, and selectively positioning a hand.

17. An arm support apparatus, comprising:

a belt adapted to fit about the waist of a patient;

a support interconnected to said belt, said support comprising a hip plate, a movable bar, and receiver;

an arm support having a post extending therefrom, said arm support having a first end adapted to generally coincide with the patient's elbow and a second end adapted to generally coincide with the patient's hand, wherein no portion of said arm support is adapted to contact the patient's upper arm such that the patient's lower arm is not mechanically interconnected to the patient's upper arm and the patient's upper arm is not mechanically interconnected to the patient's upper torso, wherein movement of the patient's lower arm relative to the patient's upper arm is not restricted, said post comprising a first end interconnected to said arm support and a second end interconnected to a lower portion, wherein said first end and said second end define ends of a cylinder having a longitudinal axis, wherein said lower portion includes an upper surface spaced from a lower surface to define a circular plate with an outer diameter greater than an outer diameter of said cylinder, said circular plate being generally perpendicular to said longitudinal axis of said cylinder, wherein said post is selectively and operatively interconnected to said receiver such that when interconnected said arm support is not statically interconnected to said receiver and said post is able to rotate within said receiver generally about said longitudinal axis of said cylinder;

wherein said receiver includes a slot for receipt of said cylinder and a cavity for receipt of said lower portion, said cavity having a bearing surface that operatively engages said lower surface of said lower portion when said post is interconnected to said receiver;

wherein said cavity is further defined by walls positioned about said slot that prevent disassociation of said post from said receiver in a direction perpendicular to said bearing surface.

a lock for maintaining the operative interconnection of said means for selectively receiving to said post of said arm support.

18. The apparatus of claim 17, wherein said bar is selectively interconnected to said hip plate and adapted to move relative thereto, and wherein said receiver is rotatably interconnected to said bar.

19. The apparatus of claim 17, wherein belt is interconnected to a hip cushion that is associated with said support.

20. The apparatus of claim 17, wherein said arm support includes a forearm portion and a hand portion, wherein at least one of said forearm portion and said arm portion being selectively deflectable and able to assume a first position of use and a second position of use.

21. The apparatus of claim 17, wherein said arm support further includes an arm strap and a wrist strap.

22. The apparatus of claim 17, wherein said arm support is selectively positionable and made of a core comprised of aluminum that is overwrapped with a cushioning material.

23. The apparatus of claim 17, further comprising a forearm portion, said forearm portion being a trough-shaped arm cuff adapted to generally contour to a patient's lower arm, said arm cuff having an inner wall and an outer wall, wherein at least one of said inner wall and said outer wall includes an indentation that is adapted to apply pressure to the patient's lower arm.

* * * * *